(12) United States Patent
Bial et al.

(10) Patent No.: US 11,793,178 B2
(45) Date of Patent: Oct. 24, 2023

(54) FUMARYLACETOACETATE HYDROLASE (FAH)-DEFICIENT AND IMMUNODEFICIENT RATS AND USES THEREOF

(71) Applicant: Yecuris Corporation, Tigard, OR (US)

(72) Inventors: John R. Bial, Portland, OR (US); Elizabeth M. Wilson, Tualatin, OR (US); Aron M. Geurts, Milwaukee, WI (US)

(73) Assignee: Yecuris Corporation, Tigard, OR (US)

( * ) Notice: Subject to any disclaimer, the term of this patent is extended or adjusted under 35 U.S.C. 154(b) by 503 days.

(21) Appl. No.: 16/557,155

(22) Filed: Aug. 30, 2019

(65) Prior Publication Data

US 2020/0008406 A1 Jan. 9, 2020

Related U.S. Application Data

(60) Division of application No. 15/159,200, filed on May 19, 2016, now Pat. No. 10,470,445, which is a continuation of application No. 14/241,316, filed as application No. PCT/US2012/052306 on Aug. 24, 2012, now abandoned.

(60) Provisional application No. 61/527,865, filed on Aug. 26, 2011.

(51) Int. Cl.
| | |
|---|---|
| *A01K 67/027* | (2006.01) |
| *C07K 14/715* | (2006.01) |
| *C12N 9/72* | (2006.01) |
| *C12N 9/14* | (2006.01) |

(52) U.S. Cl.
CPC ...... *A01K 67/0276* (2013.01); *A01K 67/0278* (2013.01); *C07K 14/7155* (2013.01); *C12N 9/14* (2013.01); *C12N 9/6462* (2013.01); *C12Y 304/21073* (2013.01); *A01K 2207/12* (2013.01); *A01K 2207/15* (2013.01); *A01K 2217/00* (2013.01); *A01K 2217/075* (2013.01); *A01K 2227/105* (2013.01); *A01K 2267/03* (2013.01); *A01K 2267/0387* (2013.01); *C12N 2750/14143* (2013.01); *C12Y 307/01002* (2013.01)

(58) Field of Classification Search
CPC ................ A01K 67/027; A01K 2227/105
See application file for complete search history.

(56) References Cited

U.S. PATENT DOCUMENTS

| | | | |
|---|---|---|---|
| 9,000,257 | B2 | 4/2015 | Grompe et al. |
| 9,314,005 | B2 | 4/2016 | Ostertag et al. |
| 2008/0313748 | A1 | 12/2008 | Tukey |
| 2009/0297486 | A1 | 12/2009 | Koliatsos et al. |
| 2010/0325747 | A1 | 12/2010 | Grompe et al. |
| 2011/0030072 | A1 | 2/2011 | Weinstein et al. |

FOREIGN PATENT DOCUMENTS

| | | |
|---|---|---|
| JP | 2010-528661 | 8/2010 |
| JP | 6484444 | 9/2014 |
| WO | 2006/090724 | 8/2006 |
| WO | 2008/151283 | 12/2008 |
| WO | 2010/127275 | 11/2010 |
| WO | 2013032918 | 3/2013 |

OTHER PUBLICATIONS

Stefan (Cell Transplantation, 1999, 8:649-659).*
Lytras (2010, Journal of International Medical Research, 38:546-557).*
Tateno (American Journal of Pathology, vol. 165, No. 3, Sep. 2004).*
Gilgenkrantz (2010, Methods in Molecular Biology, Hepatocytes, Editor Patrick Maurel, vol. 640:475-490 (22 pages).
Hickey et al. "Efficient Production of Fah-null Heterozygote Pigs by Chimeric Adeno-Associated virus-Mediated Gene Knockout and Somatic Cell Nuclear Transfer", Hepatology ePub Aug. 9, 2011, vol. 54 No. 4, pp. 1351-1359 (9 pages).
International Search Report and Written Opinion of the International Searching Authority in related application PCT/US2012/052306, dated Jan. 24, 2013 (12 pages).
Sun, et al., "Generation of human/rat xenograft animal model for the study of human donor stem cell behaviors in vivo," World J Gastroenterol, vol. 13, issue 19, May 2007, pp. 2707-2716.
Sun, et al., "Phenotypic changes of human cells in human-rat liver during partial hepatectomy-induced regernation," World J Gastroenterol, vol. 15, issue 29, Aug. 2009, pp. 3611-3620.
Ueda, et al., "Establishment of Rat Embryonic Stem Cells and Making of Chimera Rats," National Cancer Center Research Institute, PLOS One, vol. 3, issue 7, Jul. 2008, p. e2800.
Azuma, et al., "Robust expansion of human hepatocytes in Fah-/-/Rag2-/-/Il2rg-/- mice," Nat Biotechnol., vol. 25, issue 8, Aug. 2007, pp. 903-910.
Grompe, et al., "Loss of Fumarylacetoacetate Hydroloase is Reponsible for the Neonatal Hepatic Dysfunction Phenotype of Lethal Albino Mice," Genes & Development, vol. 7, pp. 2298-2307.
Locke, et al., "Generation of Humanized Animal Livers Using Embryoid Body-derived Stem Cell Transplant," Annals of Surgery, vol. 248, issue 3, Sep. 2008, pp. 487-493, abstract.
Zhang, et al., "Development of the Human/Rat chimera Model with Neonatal Rats," Dept. of Stem Cell Biology, vol. 11, issue 3, Jun. 2003, pp. 297-300, abstract.
Office Action dated Jun. 30, 2016 in related Japanese application Patent Serial No. 2014-527330 filed Aug. 24, 2012.

(Continued)

*Primary Examiner* — Valerie E Bertoglio
(74) *Attorney, Agent, or Firm* — Hovey Williams LLP

(57) ABSTRACT

Described herein are rats with a hepatic deficiency comprising decreased function, activity, or expression of an enzyme in the tyrosine catabolic pathway (such as fumarylacetoacetate hydrolase), and methods of using the same for in vivo engraftment and expansion of heterologous hepatocytes, such as human hepatocytes, analysis of human liver disease, and analysis of xenobiotics. Also disclosed is the use of immunodeficient rats for the engraftment and expansion of heterologous hepatocytes.

14 Claims, 10 Drawing Sheets

Specification includes a Sequence Listing.

(56) References Cited

OTHER PUBLICATIONS

Sun, et al., "Formation of human hepatocyte-like cells with different cellular phenotypes by human umbilical cord blood-derived cells in the human-rat chimeras," Biochem Biophys Res Commun., vol. 357, issue 4, Jun. 2007, pp. 1160-1165, abstract.
Decision of Refusal in related Japanese Patent Application Serial No. 2014-527330, dated Oct. 12, 2016 (English translation attached).
Supplementary Search Report dated Jun. 16, 2015 in related European Patent Application Serial No. 12828793.5.
Dertel, "Fetal liver cell transplantation as a potential alternative to whole liver transplantation?", J. Gastroenterol, Apr. 21, 2011, vol. 46, pp. 953-965.
Office Action dated Nov. 19, 2015 in related U.S. Appl. No. 14/241,316.
Shafritz, "A human hepatocyte factory", Nature Biotechnology, Aug. 2007, vol. 25, issue 8, pp. 871-872.
Office Action dated Sep. 22, 2016 in related European Patent Application Serial No. 12828793.5.
Office Action dated Jan. 31, 2018 in related European Patent Application Serial No. 12828793.5.
Office Action dated Feb. 7, 2018 in related Japanese Patent Application Serial No. 2017-024322 (English translation attached).
Office Action dated Feb. 21, 2018 in related Japanese Patent Application Serial No. 2014-527330 (English translation attached).
Geurts, et al., "Knockout Rats via Embryo Microinjection of Zinc-Finger Nucleases", Science, Jul. 24, 2009, vol. 325 (17 pages).
Mashimo, et al., "Generation of Knockout Rats with X-Linked Severe Combined Immunodeficiency (X-SCID) Using Zinc-Finger Nucleases", PLoS One, Jan. 2010, vol. 5, issue 1 (7 pages).
Jacob, et al., "Gene Targeting in the Rate: Advances and Opportunities", Trends Genet., Dec. 2010, vol. 26, issue 12, pp. 510-518.
Moreno, et al., "Creation and Characterization of a Renin Knockout Rat", Hypertension, 2011, vol. 57, pp. 614-619.
Office Action in corresponding Japanese Application Serial No. 2014-0527330, dated Oct. 17, 2018 (English translation attached).
Office Action in corresponding Japanese Application Serial No. 2017-024322, dated Oct. 3, 2018 (English translation attached).
Office Action in corresponding Japanese Application Serial No. 2017-024322, dated Apr. 3, 2019 (English translation attached).
Office Action in corresponding U.S. Appl. No. 15/159,200, dated Jan. 17, 2018.
Office Action in corresponding U.S. Appl. No. 15/159,200, dated Apr. 5, 2018.
Office Action in corresponding U.S. Appl. No. 15/159,200, dated Sep. 19, 2018.
Office Action in corresponding U.S. Appl. No. 15/159,200, dated May 1, 2019.
Li, 2017, Journal of Biological Chemistry, 292, 4755-4763.
Tong, 2010, Nature, 467, 211-213.
Mashimo, 2009, Current Pharmaceutical Biotechnology, 10, 214-220.
Kuijk, Scientific Reports, 6, 22154, 1-11.
Zhang, 2016, Scientific Reports, 6, 31460, 1-14.
He, 2010, Am J Pathol, 177, 1311-1319.

\* cited by examiner

Fig. 4
A.
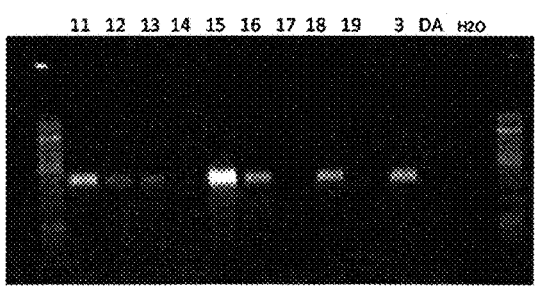
5' rFAH KO + NEO REV
Predicted MW = 2.1
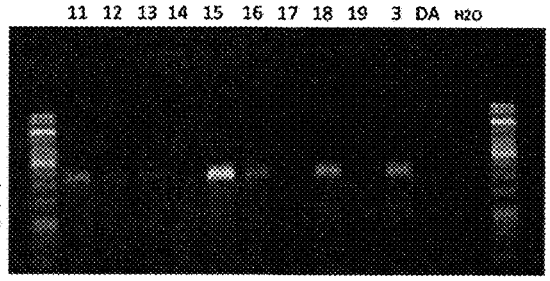
NEO FOR + 3' rFAH KO
Predicted MW = 2.1
B.
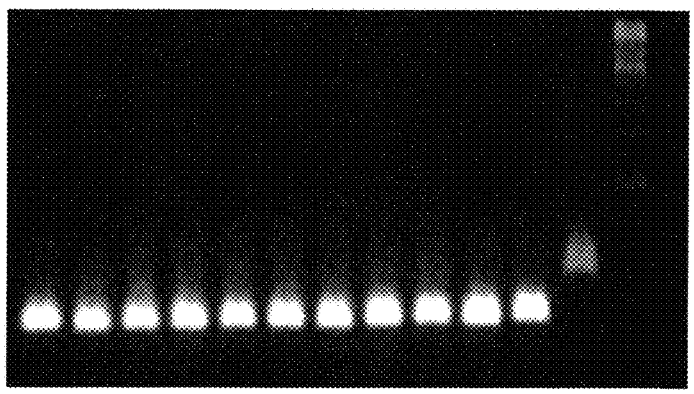
Control PCR product
Expected MW: 450 bp
Fig. 5

A.
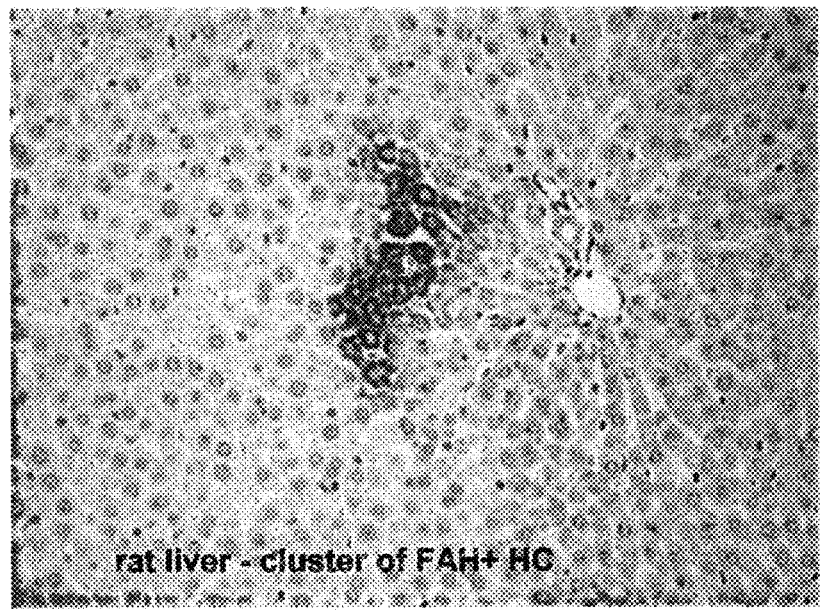
B.
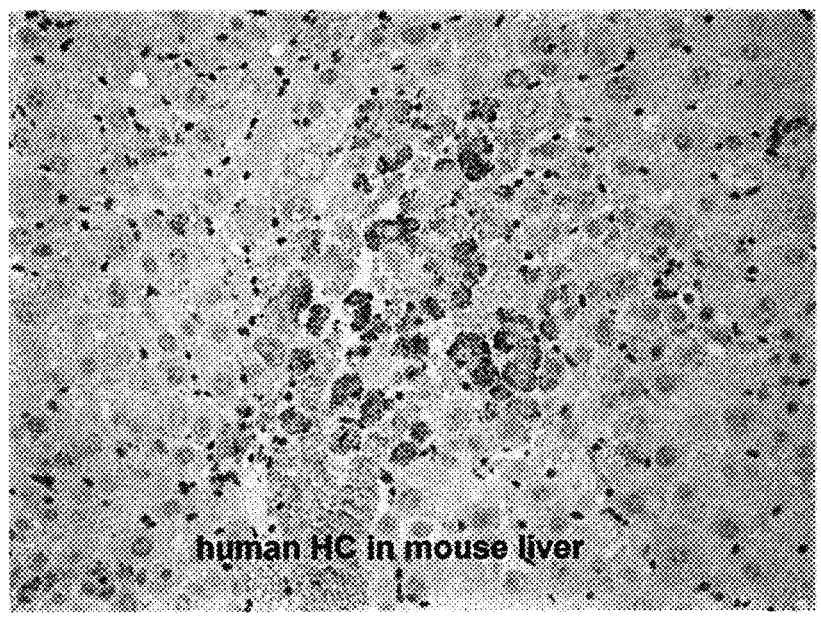
Fig. 7

```
                                                                                                    100
FAH     (1)    MSFIPVAEDSDFPIQNLPYGVFSTQSNPKPRIGVAIGDQILDLSVIKHLFTGPVLSKHQHVFDETTLNSFMGLGQAAWKEARASLQNLLSASQAQLRDDK
FAH-m1  (1)    MSFIPVAEDSDFPIQNLPYGVFSTQSNPKPRIGVAIGDQILDLSVIKHLFTGPVLSKHQHVFDETTLNSFMGLGQAAWKEARASLQNLLSASQAQLRDDK
FAH-m2  (1)    MSFIPVAEDSDFPIQNLPYGVFSTQSNPKPRIGVAIGDQILDLSVIKHLFTGPVLSKHQHVFDETTLNSF-I-GQAAWKEARASLQNLLSASQAQLRDDK
FAH-m3  (1)    MSFIPVAEDSDFPIQNLPYGVFSTQSNPKPRIGVAIGDQILDLSVIKHLFTGPVLSKHQHVFDETTLNSGME-------GGK-SILTELTVCQPS-PA

200
FAH     (101)  ELRQRAFTSQASATMHLPATIGDYTDFYSSLQHATNVGIMFRGKENALLPNWLHLPVGYHGRASSVVVSGTPIRRPMGQMRPDNSKPPVYGASKRLDMEL
FAH-m1  (99)   ELRQRAFTSQASATMHLPATIGDYTDFYSSLQHATNVGIMFRGKENALLPNWLHLPVGYHGRASSVVVSGTPIRRPMGQMRPDNSKPPVYGASKRLDMEL
FAH-m2  (90)   QR--------------------------------------------------------------------------------------------
FAH-m3  (96)   SEMTRSFGSVHSPPRLLPRCTFLLP----------------------------------------------------------------------

300
FAH     (201)  EMAFFVGPGNRFGEPIPISKAQEHIFGMVLMNDWSARDIQQWEYVPLGPFLGKSFGTTISPWVVPMDALMPFVVPNPKQDPKPLPYLCHSQPYTFDINLS
FAH-m1  (199)  EMAFFVGPGNRFGEPIPISKAQEHIFGMVLMNDWSARDIQQWEYVPLGPFLGKSFGTTISPWVVPMDALMPFVVPNPKQDPKPLPYLCHSQPYTFDINLS
FAH-m2  (92)   --------------------------------------------------------------------------------------------
FAH-m3  (121)  --------------------------------------------------------------------------------------------

400
FAH     (301)  VALKGEGMSQAATICRSNFKHMYWTILQQLTHHSVNGCNLRPGDLLASGTISGSDPESFGSMLELSWKGTKAIDVGQGQTRTFLLDGDEVIITYGHCQGDG
FAH-m1  (299)  VALKGEGMSQAATICRSNFKHMYWTILQQLTHHSVNGCNLRPGDLLASGTISGSDPESFGSMLELSWKGTKAIDVGQGQTRTFLLDGDEVIITYGHCQGDG
FAH-m2  (92)   --------------------------------------------------------------------------------------------
FAH-m3  (121)  --------------------------------------------------------------------------------------------

419
FAH     (401)  YRVGFGQCAGKVLPALSPA      SEQ ID NO:22
FAH-m1  (399)  YRVGFGQCAGKVLPALSPA      SEQ ID NO:23
FAH-m2  (92)   -------------------      SEQ ID NO:24
FAH-m3  (121)  -------------------      SEQ ID NO:25
```

Fig. 9

SEQ ID NO:26

```
Il2rg wild type  -CTCAGTGTTCCTACTCTgccccctcccagaggttcaATGCTTTGTGTTCAATGTCG
SS-Il2rg-m1    -  CTCAGTGTTCCTACTCTgccccct-------------------GTGTTCAATGTCG
SD-Il2rg-m2    -  CTCAGTGTTCCTACTCTgccccctccc-gaggttcaATGCTTTGTGTTCAATGTCG
SD-Il2rg-m3    -  CTCAGTGTTCCTACTCTgccccctcc-a-aggttcaATGCTTTGTGTTCAATGTCG Rag2 wild type -  ATGTCAGAAGCATTCTATTTCTatatgttgagatgctctgAAGATAATTCGAGTGAGG
SS-Rag2-m1     -  ATGTCAGAAGCATTCTATTTCTat--------atgctctgAAGATAATTCGAGTGAGG
SD-Rag2-m2     -  ATGTCAGAAGCATTCTATTTCTatatgtt--gatgctctgAAGATAATTCGAGTGAGG
```

Fig. 10

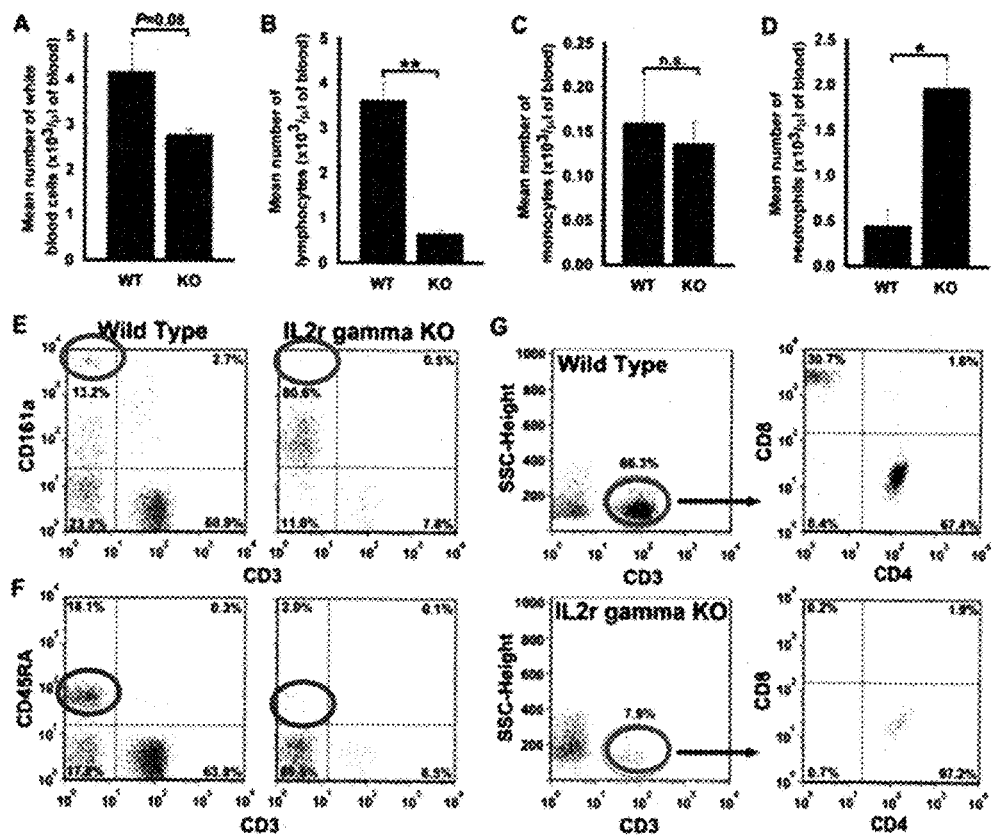

Fig. 11

| Table 1: Genotypes of offspring from heterozygous intercrosses with and without NTBC. | | | | | |
|---|---|---|---|---|---|
| | | No NTBC | | NTBC 8mg/mL | |
| GeneSymbol | GeneticStatus | Expected | Observed | Expected | Observed |
| SS-Fah-m1 | Homozygous | 26 | 0 | 26 | 35 |
| | Heterozygous | 56 | 58 | 53 | 50 |
| | Wild type | 26 | 46 | 26 | 20 |
| | | | | | |
| SS-Fah-m2 | Homozygous | 16 | 0 | 21 | 8 |
| | Heterozygous | 31 | 43 | 41 | 46 |
| | Wild type | 16 | 22 | 21 | 29 |
| | | | | | |
| SD-Fah-m3 | Homozygous | 7 | 0 | ND | ND |
| | Heterozygous | 16 | 11 | ND | ND |
| | Wild type | 7 | 19 | ND | ND |

Fah-knockout Rat
Littermate control
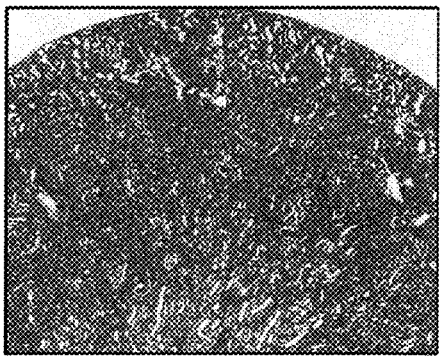
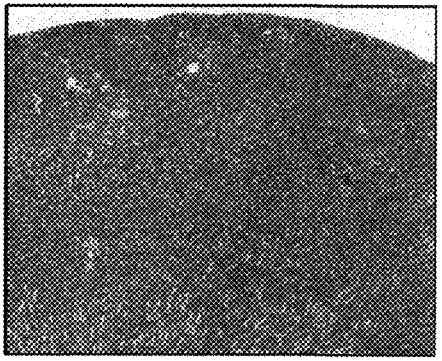
Fig. 15

FUMARYLACETOACETATE HYDROLASE (FAH)-DEFICIENT AND IMMUNODEFICIENT RATS AND USES THEREOF

CROSS-REFERENCE TO RELATED APPLICATIONS

The present application is a divisional of U.S. Ser. No. 15/159,200, filed May 19, 2016, which is a continuation of U.S. Ser. No. 14/241,316, filed Feb. 26, 2014 as the U.S. National Stage of PCT/US2012/052306, filed Aug. 24, 2012, which claims the priority benefit of U.S. Provisional Patent Application Ser. No. 61/527,865, filed Aug. 26, 2011, FUMARYLACETOACETATE HYDROLASE (FAH)-DEFICIENT ANIMALS AND USE THEREOF, each of which is incorporated by reference in its entirety herein.

STATEMENT REGARDING FEDERALLY SPONSORED RESEARCH OR DEVELOPMENT

This invention was made in part with government support under grant number 1DP2OD008396-01, awarded by the National Institutes of Health. The U.S. government has certain rights in the invention.

SEQUENCE LISTING

The nucleic and amino acid sequences listed in the accompanying sequence are presented in accordance with 37 C.F.R. 1.822. Only one strand of each nucleic acid sequence is shown, but the complementary strand is understood as included by any reference to the displayed strand. The Sequence Listing is submitted as an ASCII text file, created on Aug. 24, 2012, 22 KB, which is incorporated by reference herein. In the accompanying sequence listing: SEQ ID NO:1 is the sequence of a portion of the rat FAH protein; SEQ ID NO:2 is the nucleotide sequence of the rat Fah gene targeting cassette; SEQ ID NOs:3-20 are nucleotide sequences of primers; SEQ ID NO:21 is the nucleotide sequence of a portion of the wild type Fah rat gene; SEQ ID NO:22 is the amino acid sequence of the wild type FAH protein; SEQ ID NOs:23-25 are amino acid sequences of mutants m1-m3; SEQ ID NO:26 is the amino acid sequence of a portion of the wild type Il2rg gene; SEQ ID NO:27 is the amino acid sequence of a portion of the wild type Rag2 gene; SEQ ID NO: 28 in the amino acid sequence of SEQ ID NO:1; and SEQ ID NO:29 is the amino acid sequence of anakinra.

BACKGROUND OF THE INVENTION

Field of the Invention

The present disclosure concerns rat models having a hepatic deficiency and/or an immunodeficiency and their use. This disclosure also relates to methods of using such animal models, including expanding heterologous hepatocytes, such as human hepatocytes, in such animal models.

Description of Related Art

The liver is the principal site for the metabolism of xenobiotic compounds including medical drugs. Because many hepatic enzymes are species-specific, it is necessary to evaluate the metabolism of candidate pharmaceuticals using cultured primary human hepatocytes or their microsomal fraction. While microsomal hepatocyte fractions can be used to elucidate some metabolic functions, other tests depend on living hepatocytes. Some compounds, for example, induce hepatic enzymes and thus their metabolism changes with time. To analyze enzyme induction, hepatocytes must be not only viable, but fully differentiated and functional.

Human hepatocytes are widely used by the pharmaceutical industry during preclinical drug development. Their use is mandated by the FDA as part of drug development. For drug metabolism and other studies, hepatocytes are typically isolated from cadaveric organ donors and shipped to the location where testing will be performed. The condition (viability and state of differentiation) of hepatocytes from cadaveric sources is highly variable and many cell preparations are of marginal quality. The availability of high quality human hepatocytes is further hampered by the fact that they cannot be significantly expanded in tissue culture. After plating, the cells survive but do not divide. Hepatocytes from readily available mammalian species, such as the mouse, are not suitable for drug testing because they have a different complement of metabolic enzymes and respond differently in induction studies. Immortal human liver cells (hepatomas) or fetal hepatoblasts are also not an adequate replacement for fully differentiated adult cells. Human hepatocytes are also necessary for studies in the field of microbiology. Many human viruses, such as viruses that cause hepatitis, cannot replicate in any other cell type.

Moreover, bioartificial liver assist devices, which use hepatocytes ex vivo, have been used to support patients in acute liver failure. In addition, several clinical trials of hepatocyte transplantation have been carried out, which provided proof-of-principle that hepatocyte transplantation can be beneficial. Currently, human hepatocytes cannot be expanded significantly in culture. Hepatocytes derived from stem cells in culture are immature and generally lack full functionality. Therefore, all hepatocytes in use today are derived from human donors, either cadaveric or surgical specimens, which significantly limits hepatocyte availability. If enough human hepatocytes were available, bioartificial liver assist devices would become a viable technology and human hepatocyte transplantation could find widespread use. Given these limitations, methods of expanding primary human hepatocytes are highly desirable. There is also a need in the animal health industry for processes to expand hepatocytes from other species, such as dogs, horses, etc. for research and study.

SUMMARY

Described herein are rats that have utility for a variety of purposes, including for the expansion of hepatocytes from other species (particularly humans), and as animal models of liver diseases, including cirrhosis, hepatocellular carcinoma and hepatic infection. In general, the rats have dysfunctional livers ("hepatic deficiency"), induced liver damage, and/or an immunodeficiency, as described in more detail herein.

Provided herein are methods of expanding heterologous hepatocytes, and particularly human hepatocytes in vivo. In some embodiments, the method includes transplanting heterologous hepatocytes (or hepatocyte progenitors) into an Fah-deficient rat and allowing the heterologous hepatocytes to expand. In some cases, the Fah-deficient rat is immunosuppressed or immunodeficient. In some embodiments, the Fah-deficient rat is administered a vector encoding urokinase prior to transplantation of the heterologous hepatocytes.

Also provided are methods of expanding heterologous hepatocytes in vivo by transplanting heterologous hepatocytes (or hepatocyte progenitors) into an immunodeficient rat and allowing the heterologous hepatocytes to expand. In some embodiments, the heterologous hepatocytes are allowed to expand for at least about 2, 4, 5, 6, 7, 8, weeks, or several months.

Isolated hepatocytes (such as human hepatocytes) expanded in and collected from Fah-deficient and/or immunodeficient rats are also provided by the present disclosure.

Also provided are genetically modified rats whose genomes are homozygous for a disruption in the Fah gene such that the disruption results in loss of expression of functional FAH protein, wherein the rats exhibit decreased liver function. In some examples, the Fah-deficient rats further include transplanted heterologous hepatocytes. In some cases, the Fah-deficient rat is immunosuppressed.

Further provided are isolated rat embryonic stem cells comprising a disruption in the Fah gene.

Also provided are methods of producing an Fah-deficient rat cell by various methods including homologous recombination using the AAV-DJ vector, as well as TALENs.

Methods of using the rat models for in vivo analysis of human liver disease, drug candidates, and xenobiotics are also provided.

The foregoing and other features and advantages will become more apparent from the following detailed description of several embodiments, which proceeds with reference to the accompanying figures.

BRIEF DESCRIPTION OF THE FIGURES

FIG. 4 is a schematic of the rFah gene with the integrated targeted KO cassette containing the PGK:NEO sequence. The arrows indicate the primer binding sites and the brackets indicate the entire PCR product. The 5' and 3' PCR primer pairs contain one primer that annealed to the rFah gene outside of the targeted sequence and a second primer that annealed to the PGK:NEO sequence. Each PCR reaction contained 0.1 ng of gDNA and 2 µM of each PCR primer. Denaturing, annealing and extension temperatures along with cycle numbers were optimized for each primer set;

FIG. 5 shows (A) a photograph of the 5' and 3' PCR reactions for each potential rFah KO ES clone 11-19. The predicted molecular weights of each primer pair are indicated. Clones 14, 17 and 19 do not appear to contain the integrated rFah KO cassette; and (B) a photograph of PCR products from all of the ES clones using rFah primers outside of the integration site;

FIG. 7 shows images of (A) FAH positive staining (red) of a cluster of human hepatocytes inside the liver of rat 29; and (B) FAH positive staining (red) of human hepatocytes inside the liver of FRG KO mouse control;

FIG. 9 is the amino acid sequence of the wild type and mutations identified in Example 6 SEQ ID NOs:22-25);

FIG. 10 is the TALENs targeting coding sequences of the rat Rag2 and the chromosome X-linked Il2rg genes injected into SS and SD embryos to disrupt both genes in both strains in Example 6 (SEQ ID NO:26). The wild type sequence of each target site is shown with the TALEN monomer binding sites underlined;

FIGS. 11 and 12 show immune phenotyping of null animals (SS-Il2rg-m1$^{-/y}$ and SS-Rag2-m1$^{-/-}$ males) revealing deficiencies of CD3+ T-cells (green circles), CD45RA+ B-cells (blue circles) in both strains, and CD3-/CD161a$^{HIGH}$ NK-cells (red circles) specifically in the Il2rg null animals;

FIG. 15 is Trichrome staining of fixed tissue from a 9-week old SS-Fah-m1$^{-/-}$ after 8 days of NTBC withdrawal showing evidence of early stages of renal injury compared to a control SS inbred animal of a similar age on NTBC.

DETAILED DESCRIPTION

I. Terms and Methods

Figure 1:
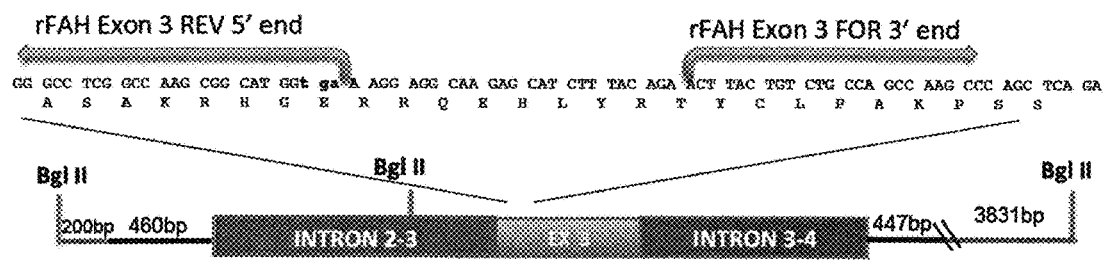
FIG. 1 is a schematic of the wild type rFAH gene including intron 2-3 and intron 3-4, along with the nucleotide sequence (SEQ ID NO:1) with corresponding amino acid sequence (SEQ ID NO:28) and PCR primers. The sequences adjacent the introns in the schematic indicate the sequence included in the rFah KO targeting cassette. The outside sequences indicate sequences that lie outside of the target sequence, but are part of the rFah gene.

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). In order to facilitate review of the various embodiments of the disclosure, the following explanations of specific terms are provided:

AAV-DJ vector: An adeno-associated virus (AAV) packaging helper that expresses a hybrid capsid containing AAV2, AAV5 and AAV8 capsid proteins and the AAV2 rep protein. (Grimm et al., *J Virol* 82:5887, 2008; U.S. Pat. No. 7,588,772; U.S. Patent Application Publication No. 2010/0047174).

Administration: To provide or give a subject an agent, such as a therapeutic agent, by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

Agent that inhibits or prevents or avoids the development of liver disease: A compound or composition that when administered to an Fah-deficient rat, prevents, avoids, delays or inhibits the development of liver disease in the animal. Liver disease or liver dysfunction is characterized by any one of a number of signs or symptoms, including, but not limited to an alteration in liver histology (such as necrosis, inflammation, fibrosis, dysplasia or hepatic cancer), an alteration in levels of liver-specific enzymes and other proteins (such as aspartate aminotransferase, alanine aminotransferase, bilirubin, alkaline phosphatase and albumin), plasma or urinary succinylacetone (SA), or generalized liver failure. In some embodiments, the agent that inhibits liver disease is a pharmacologic inhibitor of 4-OH-phenylpyruvate dioxygenase, such as 2-(2-nitro-4-trifluoro-methyl-benzoyl)-1,3 cyclohexanedione (NTBC) or methyl-NTBC. In one non-limiting example, the agent that inhibits liver disease is NTBC.

Anakinra: An interleukin-1 (IL-1) receptor antagonist. Anakinra blocks the biologic activity of naturally occurring IL-1 by competitively inhibiting the binding of IL-1 to the IL-1 receptor, which is expressed in many tissues and organs. IL-1 is produced in response to inflammatory stimuli and mediates various physiologic responses, including inflammatory and immunologic reactions. Anakinra is a recombinant, non-glycosylated version of human IL-1RA (IL-1 receptor antagonist) prepared from cultures of genetically modified *Escherichia coli*. The anakinra protein is 153 amino acids and has a molecular weight of approximately 17.3 kD and differs from native human IL-1RA in that it has a single methionine residue on its amino terminus (the amino acid sequence of anakinra is set forth herein as SEQ ID NO:29). Anakinra is also known as KINERET™.

Azathioprine: An immunosuppressant that is a purine synthesis inhibitor, inhibiting the proliferation of cells, especially leukocytes. This immunosuppressant is often used in the treatment of autoimmune diseases or organ transplant rejection. It is a pro-drug, converted in the body to the active metabolites 6-mercaptopurine (6-MP) and 6-thioinosinic acid. Azathioprine is produced by a number of generic manufacturers and as branded names (Azasan™ by Salix; Imuran™ by GlaxoSmithKline; Azamun™; and Imurel™).

Biological sample: A sample obtained from cells, tissue or bodily fluid of a subject, such as peripheral blood, serum, plasma, cerebrospinal fluid, bone marrow, urine, saliva, tissue biopsy, surgical specimen, and autopsy material. Also referred to herein as a "sample."

Cirrhosis: Refers to a group of chronic liver diseases characterized by loss of the normal microscopic lobular architecture and regenerative replacement of necrotic parenchymal tissue with fibrous bands of connective tissue that eventually constrict and partition the organ into irregular nodules. Cirrhosis has a lengthy latent period, usually followed by sudden abdominal pain and swelling with hematemesis, dependent edema, or jaundice. In advanced stages there may be ascites, pronounced jaundice, portal hypertension, varicose veins and central nervous system disorders that may end in hepatic coma.

Collecting: As used herein, "collecting" expanded heterologous hepatocytes refers to the process of removing the expanded hepatocytes from a rat that has been injected or transplanted with isolated heterologous hepatocytes (also referred to as a recipient rat). Collecting optionally includes separating the hepatocytes from other cell types. In one embodiment, the expanded heterologous hepatocytes are collected from the liver of a rat.

Common-γ chain of the interleukin receptor (Il2rg): A gene encoding the common gamma chain of interleukin receptors. Il2rg is a component of the receptors for a number of interleukins, including IL-2, IL-4, IL-7 and IL-15 (Di Santo et al. *Proc. Natl. Acad. Sci. U.S.A.* 92:377-381, 1995). Animals deficient in Il2rg exhibit a reduction in B cells and T cells and lack natural killer cells. Also known as interleukin-2 receptor gamma chain.

Cryopreserved: As used herein, "cryopreserved" refers to a cell (such as a hepatocyte) or tissue that has been preserved or maintained by cooling to low sub-zero temperatures, such as 77 K or −196° C. (the boiling point of liquid nitrogen). At these low temperatures, any biological activity, including the biochemical reactions that would lead to cell death, is effectively stopped.

Cyclosporin A: An immunosuppressant compound that is a non-ribosomal cyclic peptide of 11 amino acids produced by the soil fungus *Beauveria nivea*. Cyclosporin A is used for the prophylaxis of graft rejection in organ and tissue transplantation. Cyclosporin A is also known as cyclosporine and ciclosporin.

Decreased liver function: An abnormal change in any one of a number of parameters that measure the health or function of the liver. Decreased liver function is also referred to herein as "liver dysfunction." Liver function can be evaluated by any one of a number of means well known in the art, such as, but not limited to, examination of liver histology and measurement of liver enzymes or other proteins. For example, liver dysfunction can be indicated by necrosis, inflammation, fibrosis, oxidative damage or dysplasia of the liver. In some instances, liver dysfunction is indicated by hepatic cancer, such as hepatocellular carcinoma. Examples of liver enzymes and proteins that can be tested to evaluate liver dysfunction include, but are not limited to, alanine aminotransferase (ALT), aspartate aminotransferase (AST), bilirubin, alkaline phosphatase and albumin. Liver dysfunction also can result in generalized liver failure. Procedures for testing liver function are well known in the art, such as those taught by Grompe et al. (*Genes Dev.* 7:2298-2307, 1993) and Manning et al. (*Proc. Natl. Acad. Sci. U.S.A.* 96:11928-11933, 1999).

Deficient: As used herein, "Fah-deficient" or "deficient in Fah" refers to an animal, such as a rat, having a substantial decrease in, or the absence of, FAH enzyme production or activity, for example an animal having a disruption in the Fah gene (such as an insertion, deletion or one or more point mutations), which results in a substantial decrease in, or the absence of, Fah mRNA expression and/or functional FAH enzyme activity. As used herein, the term "loss of expression" of functional FAH protein does not refer to only a complete loss of expression, but also includes a substantial decrease in expression of functional FAH protein, such as a decrease of about 80%, about 90%, about 95% or about 99%. In some embodiments, the Fah-deficient rat comprises heterozygous or homozygous insertions in the Fah gene (such as an insertion that includes an in-frame stop codon), with homozygous insertions being particularly preferred. In some embodiments, the insertion is in exon 3 of Fah. In some embodiments, the Fah-deficient rat comprises heterozygous or homozygous deletions in the Fah gene, with homozygous deletions being particularly preferred. As one example, the deletion is in exon 3 of Fah. In another embodiment, the Fah-deficient rat comprises one or more point mutations in the Fah gene. Examples of suitable Fah point mutations are known in the art (see, e.g., Aponte et al. *Proc. Natl. Acad. Sci. U.S.A.* 98(2):641-645, 2001).

Deplete: To reduce or remove. For example, "macrophage depletion" refers to the process of eliminating, removing, reducing or killing macrophages in an animal. An animal that has been depleted of macrophages is not necessarily completely devoid of macrophages but at least exhibits a reduction in the number or activity of macrophages. In one embodiment, macrophage depletion results in at least a 10%, at least a 25%, at least a 50%, at least a 75%, at least a 90% or a 100% reduction in functional macrophages.

Disruption: As used herein, a "disruption" in a gene refers to any insertion, deletion or point mutation, or any combination thereof. In some embodiments, the disruption leads to a partial or complete loss of expression of mRNA and/or functional protein.

Engraft: To implant cells or tissues in an animal. As used herein, engraftment of heterologous hepatocytes in a recipient rat refers to the process of heterologous hepatocytes becoming implanted in the recipient rat following injection. Engrafted heterologous hepatocytes are capable of expansion in the recipient rat.

Expand: To increase in quantity. As used herein, "expanding" heterologous hepatocytes refers to the process of allowing cell division to occur such that the hepatocytes actively proliferate in vivo and the number of heterologous hepatocytes increases as compared to the original number of heterologous hepatocytes transplanted into the recipient rat.

Fetus: The unborn offspring of an animal in the postembryonic period.

FK506: FK506, also known as tacrolimus or fujimycin, is an immunosuppressant drug. FK506 a 23-membered macrolide lactone first discovered in the fermentation broth of a Japanese soil sample that contained the bacteria *Streptomyces tsukubaensis*. This compound is often used after allogeneic organ transplant to reduce the activity of the patient's immune system and lower the risk of organ rejection. FK506 reduces T-cell and interleukin-2 activity. It is also used in a topical preparation in the treatment of severe atopic dermatitis (eczema), severe refractory uveitis after bone marrow transplants, and the skin condition vitiligo.

Fludarabine: A purine analog that inhibits DNA synthesis. Fludarabine is often used as a chemotherapeutic drug for the treatment of various hematologic malignancies.

FRG KO mouse: A mutant mouse having homozygous deletions in the fumarylacetoacetate hydrolase (Fah), recombination activating gene 2 (Rag2) and hemizygous or homozygous deletions of common-γ chain of the interleukin receptor (Il2rg) x-linked gene. Also referred to as Fah$^{-/-}$/Rag2$^{-/-}$/Il2rg$^{-/-}$ or Fah$^{-/-}$/Rag2$^{-/-}$/Il2rg$^{-/y}$. As used herein, homozygous deletions in the Fah, Rag2 and Il2rg genes indicates no functional FAH, RAG-2 and IL-2Rγ protein is expressed in mice comprising the mutations.

Fumarylacetoacetate hydrolase (FAH): A metabolic enzyme that catalyzes the last step of tyrosine catabolism. Mice having a homozygous deletion of the Fah gene exhibit altered liver mRNA expression and severe liver dysfunction (Grompe et al. *Genes Dev.* 7:2298-2307, 1993). Point mutations in the Fah gene have also been shown to cause hepatic failure and postnatal lethality (Aponte et al. *Proc. Natl. Acad. Sci. U.S.A.* 98(2):641-645, 2001). Humans deficient for Fah develop the liver disease hereditary tyrosinemia type 1 (HT1) and develop liver failure. Fah deficiency leads to accumulation of fumarylacetoacetate, a potent oxidizing agent and this ultimately leads to cell death of hepatocytes deficient for Fah. Thus, Fah-deficient rats can be repopulated with hepatocytes from other species, including humans. Fah genomic, mRNA and protein sequences for a number of different species are publically available, such as in the GenBank database (see, for example, Gene ID 29383 (rat Fah); Gene ID 14085 (mouse Fah); Gene ID 610140 (dog FAH); Gene ID 415482 (chicken FAH); Gene ID 100049804 (horse FAH); Gene ID 712716 (rhesus macaque FAH); Gene ID 100408895 (marmoset FAH); Gene ID 100589446 (gibbon FAH); Gene ID 467738 (chimpanzee FAH); and Gene ID 508721 (cow FAH)).

Hepatic pathogen: Refers to any pathogen, such as a bacterial, viral or parasitic pathogen, that infects cells of the liver. In some embodiments, the hepatic pathogen is a "hepatotropic virus" (a virus that targets the liver), such as HBV or HCV.

Hepatocellular carcinoma (HCC): HCC is a primary malignancy of the liver typically occurring in patients with inflammatory livers resulting from viral hepatitis, liver toxins or hepatic cirrhosis.

Hepatocyte: A type of cell that makes up 70-80% of the cytoplasmic mass of the liver. Hepatocytes are involved in protein synthesis, protein storage and transformation of carbohydrates, synthesis of cholesterol, bile salts and phospholipids, and detoxification, modification and excretion of exogenous and endogenous substances. The hepatocyte also initiates the formation and secretion of bile. Hepatocytes manufacture serum albumin, fibrinogen and the prothrombin group of clotting factors and are the main site for the synthesis of lipoproteins, ceruloplasmin, transferrin, complement and glycoproteins. In addition, hepatocytes have the ability to metabolize, detoxify, and inactivate exogenous compounds such as drugs and insecticides, and endogenous compounds such as steroids.

Hepatocyte progenitor: Any cell type capable of giving rise to a hepatocyte. Examples of hepatocyte progenitors include, but are not limited to, embryonic stem cells (ESCs), induced pluripotent stem cells (IPSC), adult intrahepatic stem cells, mesenchymal stem cells and amniotic stem cells. In the context of the present disclosure, methods of expanding heterologous hepatocytes in vivo include transplanting heterologous hepatocyte or hepatocyte progenitors.

Hereditary tyrosinemia type 1 (HT1): Tyrosinemia is an error of metabolism, usually inborn, in which the body cannot effectively break down the amino acid tyrosine. HT1 is the most severe form of this disorder and is caused by a shortage of the enzyme fumarylacetoacetate hydrolase (FAH) encoded by the gene Fah found on human chromosome number 15. FAH is the last in a series of five enzymes needed to break down tyrosine. Symptoms of HT1 usually appear in the first few months of life and include failure to gain weight and grow at the expected rate (failure to thrive), diarrhea, vomiting, yellowing of the skin and whites of the eyes (jaundice), cabbage-like odor, and increased tendency to bleed (particularly nosebleeds). HT1 can lead to liver and kidney failure, problems affecting the nervous system, and an increased risk of liver cancer.

Heterologous: Derived from a source other than (i.e., foreign to) the referenced species in contrast to material derived from, naturally associated with, or native to, that species. In the case of the rat models herein, the rats can be transplanted and engrafted with hepatocytes from species other than the recipient rat, such as humans, dogs, pigs, etc.

Heterozygous: Having dissimilar alleles at corresponding chromosomal loci. For example, a rat heterozygous for a particular gene mutation has the mutation in one allele of the gene but not the other.

Homozygous: Generally means having identical alleles at one or more loci. As used herein, "homozygous" for disruptions or "homozygous" for a deficiency refers to an organism having disruptions (such as a deletion, insertion or point mutation) of both alleles of a gene, as well as "compound heterozygosity" in which the organism may have disruptions on two unrelated alleles, which nevertheless behave like a homozygous disruption, resulting in loss of functional gene products.

Humanized: As used herein, references to "humanized" animals (rats) or livers refers to animals or livers transplanted with human hepatocytes in which the human hepatocytes have expanded in vivo to substantially repopulate the liver of the animal with human hepatocytes.

Immunodeficient: Lacking in at least one essential function of the immune system. As used herein, an "immunodeficient" rat is one lacking specific components of the immune system or lacking function of specific components of the immune system (such as, for example, B cells, T cells or NK cells). In some cases, an immunodeficient rat lacks macrophages. In some embodiments, an immunodeficient rat comprises one or more genetic alterations that prevent or inhibit the development of functional immune cells (such as B cells, T cells or NK cells). In some embodiments, the genetic alteration is selected from the group consisting of recombination activating gene 1 (Rag1) deficiency, recombination activating gene 2 (Rag2) deficiency, interleukin-2 receptor gamma chain (Il2rg) deficiency, the Dnapk$^{-/-}$ (SCID) mutation, the humanized/humanized SIRP-alpha genotype, the nude rat mutation, perforin knockouts, and combinations thereof. For example, replacement of the rat Sirp-α gene with human sequence, i.e. humanization (hum) Sirp-α$^{hum/hum}$ will block activation of rat macrophages by human cells. In some embodiments, an "immunodeficient rat" comprises one or more of the following genetic alterations: Rag1$^{-/-}$, Rag2$^{-/-}$, Il2rg$^{-/y}$, SCID, SIRP-alpha genotype, perforin$^{-/-}$, and/or nude. Immunodeficient animal strains are well known in the art and are commercially available, such as from The Jackson Laboratory (Bar Harbor, ME) or Taconic (Hudson, NY). In some embodiments, the rat is a Fah$^{-/-}$/Rag2$^{-/-}$/Il2rg$^{-/-}$/Il1r1$^{-/-}$ rat, a Fah$^{-/-}$/Rag1$^{-/-}$/Il2rg$^{-/-/Il}$Il1r1$^{-/-}$ rat, a Fah$^{-/-}$/Rag2$^{-/-}$/Il2rg$^{-/-}$/Il1r1$^{-/-}$ rat, or a Fah$^{-/-}$/Rag1$^{-/-}$/Il2rg$^{-/-}$/Il1r1$^{-/-}$ rat. In some embodiments, an immunodeficient rat is an animal that has been administered one or more immunosuppressants.

Immunosuppressant: Any compound that decreases the function or activity of one or more aspects of the immune system, such as a component of the humoral or cellular immune system or the complement system. Immunosuppressants are also referred to as "immunosuppressive agents." Exemplary immunosuppressants include, but are not limited to: (1) antimetabolites, such as purine synthesis inhibitors (e.g., azathioprine and mycophenolic acid), pyrimidine synthesis inhibitors (e.g., leflunomide and teriflunomide) and antifolates (e.g., methotrexate); (2) macrolides, such as FK506, cyclosporine A and pimecrolimus; (3) TNF-α inhibitors, such as thalidomide and lenalidomide; (4) IL-1 receptor antagonists, such as anakinra; (5) mammalian target of rapamycin (mTOR) inhibitors, such as rapamycin (sirolimus), deforolimus, everolimus, temsirolimus, zotarolimus and biolimus A9; (6) corticosteroids, such as prednisone; and (7) antibodies to any one of a number of cellular or serum targets. In particular embodiments of the disclosure, the immunosuppressant is FK506, cyclosporin A, fludarabine, mycophenolate, prednisone, rapamycin or azathioprine, or combinations thereof.

Exemplary cellular targets and their respective inhibitor compounds include, but are not limited to complement component 5 (e.g., eculizumab); tumor necrosis factors (TNFs) (e.g., infliximab, adalimumab, certolizumab pegol, afelimomab and golimumab); IL-5 (e.g., mepolizumab); IgE (e.g., omalizumab); BAYX (e.g., nerelimomab); interferon (e.g., faralimomab); IL-6 (e.g., elsilimomab); IL-12 and IL-13 (e.g., lebrikizumab and ustekinumab); CD3 (e.g., muromonab-CD3, otelixizumab, teplizumab, visilizumab); CD4 (e.g., clenoliximab, keliximab and zanolimumab); CD11a (e.g., efalizumab); CD18 (e.g., erlizumab); CD20 (e.g., afutuzumab, ocrelizumab, pascolizumab); CD23 (e.g., lumiliximab); CD40 (e.g., teneliximab, toralizumab); CD62L/L-selectin (e.g., aselizumab); CD80 (e.g., galiximab); CD147/basigin (e.g., gavilimomab); CD154 (e.g., ruplizumab); BLyS (e.g., Belimumab); CTLA-4 (e.g., ipilimumab, tremelimumab); CAT (e.g., bertilimumab, lerdelimumab, metelimumab); integrin (e.g., natalizumab); IL-6 receptor (e.g., Tocilizumab); LFA-1 (e.g., odulimomab); and IL-2 receptor/CD25 (e.g., basiliximab, daclizumab, inolimomab).

Other immunosuppressive agents include zolimomab aritox, atorolimumab, cedelizumab, dorlixizumab, fontolizumab, gantenerumab, gomiliximab, maslimomab, morolimumab, pexelizumab, reslizumab, rovelizumab, siplizumab, talizumab, telimomab aritox, vapaliximab, vepalimomab, anti-thymocyte globulin, anti-lymphocyte globulin; CTLA-4 inhibitors (e.g., abatacept, belatacept); aflibercept; alefacept; rilonacept; and TNF inhibitors (e.g., etanercept).

Immunosuppression: Refers to the act of reducing the activity or function of the immune system. Immunosuppression can be achieved by administration of an immunosuppressant compound or can be the effect of a disease or disorder (for example, immunosuppression that results from HIV infection or due to a genetic defect). In some cases, immunosuppression occurs as the result of a genetic mutation that prevents or inhibits the development of functional immune cells.

Induced pluripotency stem cells (iPSC): A type of pluripotent stem cell artificially derived from a non-pluripotent cell, typically an adult somatic cell, by inducing expression of certain genes. iPSCs can be derived from any organism, such as a mammal. In some embodiments, iPSCs are produced from mice, rats, rabbits, guinea pigs, goats, pigs, cows, non-human primates or humans. Human derived iPSCs are exemplary. iPSCs are similar to ES cells in many respects, such as the expression of certain stem cell genes and proteins, chromatin methylation patterns, doubling time, embryoid body formation, teratoma formation, viable chimera formation, and potency and differentiability. Methods for producing iPSCs are known in the art. For example, iPSCs are typically derived by transfection of certain stem cell-associated genes (such as Oct-3/4 (Pouf51) and Sox2) into non-pluripotent cells, such as adult fibroblasts. Transfection can be achieved through viral vectors, such as retroviruses, lentiviruses, or adenoviruses. For example, cells can be transfected with Oct3/4, Sox2, Klf4, and c-Myc using a retroviral system or with OCT4, SOX2, NANOG, and LIN28 using a lentiviral system. After 3-4 weeks, small numbers of transfected cells begin to become morphologically and biochemically similar to pluripotent stem cells, and are typically isolated through morphological selection, doubling time, or through a reporter gene and antibiotic selection. In one example, iPSCs from adult human cells are generated by the method of Yu et al. (*Science* 318(5854): 1224, 2007) or Takahashi et al. (*Cell* 131(5):861-72, 2007). iPSCs are also known as iPS cells.

Infectious load: Refers to the quantity of a particular pathogen in a subject or in a sample from the subject. Infectious load can be measured using any one of a number of methods known in the art. The selected method will vary depending on the type of pathogen to be detected and the reagents available to detect the pathogen. Infectious load can also be measured, for example, by determining the titer of the pathogen, the method for which will vary depending on the pathogen to be detected. For example, the titer of some viruses can be quantified by performing a plaque assay. In some examples, infectious load is measured by quantifying the amount of a pathogen-specific antigen in a sample. In other examples, infectious load is measured by quantifying the amount of a pathogen-specific nucleic acid molecule in a sample. Quantifying encompasses determining a numerical value or can be a relative value.

Isolated: An "isolated" biological component, such as a nucleic acid, protein (including antibodies) or organelle, has been substantially separated or extracted away from other biological components in the environment (such as a cell) in which the component naturally occurs, i.e., other chromosomal and extra-chromosomal nucleic acids, adjacent sequences, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids. In either case, "isolated" nucleic acids and/or proteins result in new chemical entities not found in nature.

Mammalian target of rapamycin (mTOR) inhibitor: A molecule that inhibits expression or activity of mTOR. mTOR inhibitors include, but are not limited to small molecule, antibody, peptide and nucleic acid inhibitors. For example, an mTOR inhibitor can be a molecule that inhibits the kinase activity of mTOR or inhibits binding of mTOR to a ligand. Inhibitors of mTOR also include molecules that down-regulate expression of mTOR. A number of mTOR inhibitors are known in the art, including rapamycin (sirolimus).

Mycophenolate: An immunosuppressant typically used to prevent rejection of allogeneic transplants. This drug is generally administered orally or intravenously. Mycophenolate is derived from the fungus *Penicillium stoloniferum*. Mycophenolate mofetil, the pro-drug form, is metabolized in the liver to the active moiety mycophenolic acid. It inhibits inosine monophosphate dehydrogenase, the enzyme that controls the rate of synthesis of guanine monophosphate in the de novo pathway of purine synthesis used in the proliferation of B and T lymphocytes. Mycophenolic acid is commonly marketed under the trade names CellCept™ (mycophenolate mofetil; Roche) and Myfortic™ (mycophenolate sodium; Novartis).

NTBC (2-nitro-4-trifluoro-methyl-benzoyl)-1,3 cyclohexanedione, also known as nitisinone): An inhibitor of 4-hydroxy-phenylpyruvate dioxygenase (HPPD). HPPD catalyzes the conversion of 4-hydroxyphenylpyruvate to homogentisate, the second step in tyrosine catabolism. Treatment with NTBC blocks the tyrosine catabolism pathway at this step and prevents the accumulation of succinylacetone, a pathognomonic metabolite that accumulates in Fah-deficient humans and animals.

Nude rat: Refers to a rat strain with a genetic mutation that causes a deteriorated or absent thymus, resulting in an inhibited immune system due to a greatly reduced number of T cells.

Prednisone: A synthetic corticosteroid that is an effective immunosuppressant. It is often used to treat certain inflammatory diseases, autoimmune diseases and cancers as well as treat or prevent organ transplant rejection. Prednisone is usually taken orally but can be delivered by intramuscular injection or intravenous injection. It is a prodrug that is converted by the liver into prednisolone, which is the active drug and also a steroid.

Rapamycin: A compound with known immunosuppressive and anti-proliferative properties. Rapamycin, also known as sirolimus, is a macrolide that was first discovered as a product of the bacterium *Streptomyces hygroscopicus*. Rapamycin binds and inhibits the activity of mTOR.

Recipient: As used herein, a "recipient rat" is a rat that has been injected with heterologous hepatocytes as described herein. Typically, a portion (the percentage can vary) of the heterologous hepatocytes engraft in the recipient rat. In some embodiments, the recipient rat is immunosuppressed or immunodeficient. In some embodiments, the recipient rat is Fah-deficient.

Recombination activating gene 1 (Rag1): A gene involved in activation of immunoglobulin V(D)J recombination. The RAG1 protein is involved in recognition of the DNA substrate, but stable binding and cleavage activity also requires RAG2. Rag-1-deficient rats have no mature B and T lymphocytes.

Recombination activating gene 2 (Rag2): A gene involved in recombination of immunoglobulin and T cell receptor loci. Rats deficient in the Rag2 gene are unable to undergo V(D)J recombination, resulting in a complete loss of functional T cells and B cells (Shinkai et al. *Cell* 68:855-867, 1992).

Serial transplantation: The process for expanding heterologous hepatocytes in vivo in which hepatocytes expanded in a first animal are collected and transplanted, such as by injection, into a secondary animal for further expansion. Serial transplantation can further include tertiary, quaternary or additional animals.

Somatic cell nuclear transfer (SCNT): A laboratory technique for creating a clonal embryo, using an ovum with a donor nucleus. In SCNT, the nucleus of a somatic cell is removed and the rest of the cell discarded. At the same time, the nucleus of an egg cell is removed. The nucleus of the somatic cell is then inserted into the enucleated egg cell. After being inserted into the egg, the somatic cell nucleus is reprogrammed by the host cell. The egg, now containing the nucleus of a somatic cell, is stimulated with a shock and will begin to divide. After many mitotic divisions in culture, this single cell forms a blastocyst with almost identical DNA to the original organism.

Stem cell: A cell having the unique capacity to produce unaltered daughter cells (self-renewal; cell division produces at least one daughter cell that is identical to the parent cell) and to give rise to specialized cell types (potency). Stem cells include, but are not limited to, embryonic stem (ES) cells, embryonic germ (EG) cells, germline stem (GS) cells, human mesenchymal stem cells (hMSCs), adipose tissue-derived stem cells (ADSCs), multipotent adult progenitor cells (MAPCs), multipotent adult germline stem cells (maGSCs) and unrestricted somatic stem cell (USSCs). The role of stem cells in vivo is to replace cells that are destroyed during the normal life of an animal. Generally, stem cells can divide without limit. After division, the stem cell may remain as a stem cell, become a precursor cell, or proceed to terminal differentiation. A precursor cell is a cell that can generate a fully differentiated functional cell of at least one given cell type. Generally, precursor cells can divide. After division, a precursor cell can remain a precursor cell, or may proceed to terminal differentiation. In one embodiment, the stem cells give rise to hepatocytes.

Therapeutic agent: A chemical compound, small molecule, or other composition, such as an antisense compound, antibody, protease inhibitor, hormone, chemokine or cytokine, capable of inducing a desired therapeutic or prophylactic effect when properly administered to a subject. As used herein, a "candidate agent" is a compound selected for screening to determine if it can function as a therapeutic agent for a particular disease or disorder.

Titer: In the context of the present disclosure, titer refers to the amount of a particular pathogen in a sample.

Tolerance: A state of unresponsiveness to a specific antigen or group of antigens to which a subject (such as a human or animal) is normally responsive. Immune tolerance is achieved under conditions that suppress the immune reaction and is not just the absence of an immune response. Immune tolerance can result from a number of causes including prior contact with the same antigen in fetal life or in the newborn period when the immune system is not yet mature; prior contact with the antigen in extremely high or low doses; exposure to radiation, chemotherapy drugs, or other agents that impair the immune system; heritable diseases of the immune system; and acquired diseases of the immune system.

Toxin: In the context of the present disclosure, "toxin" refers to any poisonous substance, including any chemical toxin or biological toxin.

Transgene: An exogenous nucleic acid sequence introduced into a cell or the genome of an organism.

Transplant or transplanting: Refers to the process of grafting an organ, tissue or cells from one subject (e.g., human or animal) to another subject, or to another region of the same subject.

Urokinase: Also called urokinase-type Plasminogen Activator (uPA), urokinase is a serine protease. Urokinase was originally isolated from human urine, but is present in several physiological locations, such as the blood stream and the extracellular matrix. The primary physiological substrate is plasminogen, which is an inactive zymogen form of the serine protease plasmin. Activation of plasmin triggers a proteolytic cascade which, depending on the physiological environment, participates in thrombolysis or extracellular matrix degradation. In one embodiment of the methods provided herein, urokinase is administered to a recipient rat prior to hepatocyte injection. In some embodiments, urokinase is human urokinase. In some embodiments, the human urokinase is the secreted form of urokinase. In some embodiments, the human urokinase is a modified, non-secreted form of urokinase (see U.S. Pat. No. 5,980,886).

Vector: A nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An integrating vector is capable of integrating itself into a host nucleic acid. An expression vector is a vector that contains the necessary regulatory sequences to allow transcription and translation of inserted gene or genes.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the term "and/or" when used in a list of two or more items, means that any one of the listed items can be employed by itself or any combination of two or more of the listed items can be employed. For example, if a composition comprises or excludes components A, B, and/or C, the composition can contain or exclude A alone; B alone; C alone; A and B in combination; A and C in combination; B and C in combination; or A, B, and C in combination. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

II. Overview of Several Embodiments

Described herein are genetically modified rats (*Rattus* sp.), which have utility for a variety of purposes, including for the expansion of hepatocytes from other species (particularly humans), and as animal models of liver diseases and normal liver pathology, including intermediate metabolism, bile acid production, small molecule transporters, assessment of biologics, drug metabolism, pharmacokinetics, as well as cirrhosis, hepatocellular carcinoma, hepatic infection, hepatic toxicity, gene therapy, liver regeneration, alcoholic liver disease, fatty liver disease, metabolic liver disease, and the like. The term "rat," as used herein, is specific to the genus *Rattus*, and expressly does not encompass mice species (*Mus* sp.).

In one or more embodiments, the rats are Fah-deficient, and preferably comprise a genome that is homozygous for a disruption in the Fah gene, such that the disruption results in loss of expression of functional FAH protein resulting in decreased liver function. The Fah gene disruption need not result in a complete loss of expression of functional FAH protein. In some examples, loss or decrease of expression, activity, or function, of functional FAH protein is loss of expression of about 80%, about 90%, about 95% or about 99% of functional protein. The Fah gene disruption can be any modification that results in a significant diminishment (reduction) or complete loss of expression of functional FAH protein. In some embodiments, the disruption is an insertion, a deletion, or one or more point mutations in the Fah gene, or any combination thereof. For example, the disruption can be an insertion that includes an in-frame stop codon. The insertion can also include additional nucleic acid sequences, such as nucleic acid encoding a selectable marker. In particular examples, the Fah-deficient rat is homozygous for disruptions in exon 3 of the Fah gene. Further provided are isolated rat embryonic stem (ES) cells comprising a disruption in the Fah gene.

Also provided herein is a method of producing an Fah-deficient rat cell (such as an embryonic stem cell) by transfecting the rat cell with an AAV-DJ targeting vector, wherein the targeting vector comprises a targeting cassette comprising 5' and 3' homology arms that target a portion of the rat Fah gene (such as exon 3 of the Fah gene) and which flank a nucleic acid sequence (such as nucleic acid sequence encoding an antibiotic resistance gene), such that following transfection of the cell with the targeting vector, homologous recombination occurs, replacing the targeted portion of the rat Fah gene with the targeting cassette, thereby producing an Fah-deficient rat cell.

In some embodiments, an immunodeficient rat is provided. The immunodeficiency of the mouse can be due to a genetic alteration, immunosuppression, or a combination thereof. In one or more embodiments, the rat lacks functional T cells, B cells, and/or NK cells.

In some embodiments, the rat is immunosuppressed. In some examples, immunosuppression is the result of administration of one or more immunosuppressive agents. Any suitable immunosuppressive agent or agents effective for achieving immunosuppression in the rat can be used. Examples of immunosuppressive agents include, but are not limited to, FK506, cyclosporin A, fludarabine, mycophenolate, prednisone, rapamycin and azathioprine. Combinations of immunosuppressive agents can also be administered.

In other embodiments, the immunodeficiency is the result of one or more genetic alterations that result in a lack of a specific component of the immune system, or a lack of functionality of a specific component of the immune system (such as a lack of functional B, T and/or NK cells). In some examples, the one or more genetic alterations comprise a genetic alteration of the Rag2 gene or a genetic alteration of the Il2rg gene such that the genetic alteration results in loss of expression of functional RAG-2 protein or IL-2Rγ protein. In one example, the one or more genetic alterations comprise a genetic alteration of the Rag2 gene and a genetic alteration of the Il2rg gene. In some cases, the genetic alteration comprises homozygous deletions in the Rag2 gene or the Il2rg gene. Such deletions, in combination with the Fah-deficiency result in an FRG KO rat. In other examples, the genetic alteration is SCID, NOD, or nude. Specific cells of the immune system (such as macrophages or NK cells) can also be depleted. Methods of depleting particular cell types are known in the art.

In one or more embodiments, the rat comprises heterologous hepatocytes, such as human hepatocytes. It will be appreciated that a significant advantage of the invention is that the heterologous hepatocytes have not just been transplanted/engrafted in the rat, but expanded (i.e., actively proliferated) in the rat. In other words, various embodiments of the invention are concerned with rats having humanized livers.

Methods of expanding heterologous hepatocytes in vivo are also provided. In some embodiments, the method includes transplanting heterologous hepatocytes (or hepatocyte progenitors) into an Fah-deficient rat and allowing the heterologous hepatocytes to expand. In other embodiments, the method includes transplanting heterologous hepatocytes into an immunodeficient rat and allowing the heterologous hepatocytes to expand. In yet other embodiments, the method includes transplanting heterologous hepatocytes into an Fah-deficient and immunodeficient rat and allowing the heterologous hepatocytes to expand. In other embodiments, the method includes transplanting heterologous hepatocytes into a rat with a hepatic deficiency, such as decreased expression, activity, or function of an enzyme in the tyrosine catabolic pathway, and allowing the heterologous hepatocytes to expand.

In some embodiments, the heterologous hepatocytes are transplanted by injection into the hepatic artery, spleen, portal vein, peritoneal cavity, hepatic tissue mass, or lymphatic system of the rat. In some embodiments, the heterologous hepatocytes (or hepatocyte progenitors) transplanted into the rat are isolated human hepatocytes (or hepatocyte progenitors). In some embodiments, the heterologous hepatocytes are transplanted as part of a liver tissue graft. The isolated heterologous hepatocytes can be obtained from any one of a number of different mammals as well as different sources. Mammalian hepatocytes can be obtained from dogs, pigs, horses, rabbits, mice, marmoset, woodchuck, non-human primates, and humans. In one embodiment, the heterologous hepatocytes are isolated from the liver of a human or non-human organ donor. In another embodiment, the heterologous hepatocytes are isolated from a surgical resection. In another embodiment, the heterologous hepatocytes are derived from a stem cell, such as an embryonic stem cell, an induced pluripotency stem cell, a mesenchymal-derived stem cell, an adipose tissue-derived stem cell, a multipotent adult progenitor cell, an unrestricted somatic stem cell or tissue-specific liver stem cell, which can be found in the liver itself, the gall bladder, the intestine, the pancreas, or salivary glands. In another embodiment, the heterologous hepatocytes are derived from monocytes or amniocytes, thus a stem cell or progenitor cell is obtained in vitro to produce hepatocytes. In another embodiment, the heterologous hepatocytes are derived by reprogramming a distinct cell lineage such as a skin fibroblast, keratinocyte or lymphocyte. In another embodiment, the heterologous hepatocytes have been cryopreserved prior to injection (i.e., are from cryopreserved lots which are thawed). In some embodiments, human hepatocytes can be isolated from humanized mice, pigs, or other rats, as discussed in more detail herein.

In some embodiments, the one or more immunosuppressive agents (discussed above) are administered to the rat at least about 2 days prior to heterologous hepatocyte transplantation. Immunosuppression may be continued after transplantation for a period of time, for example for a portion of or the entire life of the rat.

It will be appreciated that various models of liver injury may be used in the rat to facilitate hepatocyte engraftment and expansion, including, without limitation, inducible injury and/or genetic modifications (e.g., Fah disruption, uPA, TK-NOG (Washburn et al., *Gastroenterology*, 140(4): 1334-44, 2011), albumin AFC8, albumin diphtheria toxin, Wilson's Disease, and the like). Combinations of liver injury techniques may also be used. In some embodiments, the rat is administered a vector encoding a urokinase gene prior to injection of the heterologous hepatocytes. In one embodiment, the urokinase gene is human urokinase. Wild-type urokinase is a secreted protein. Thus, in some embodiments, the human urokinase is a secreted form of urokinase (Nagai et al., *Gene* 36:183-188, 1985). In some embodiments, the human urokinase is a modified, non-secreted form of urokinase. For example, Lieber et al. (*Proc. Natl. Acad. Sci.* 92:6210-6214, 1995) describe non-secreted forms of urokinase generated by inserting a sequence encoding an endoplasmic reticulum retention signal at the carboxyl terminus of urokinase, or by replacing the pre-uPA signal peptide with the amino-terminal RR-retention signal (Strubin et al., *Cell* 47:619-625, 1986; Schutze et al., *EMBO J.* 13:1696-1705, 1994) and the transmembrane anchor separated by a spacer peptide from the membrane II protein Iip33 (Strubin et al., *Cell* 47:619-625, 1986). Non-secreted forms of urokinase are also described in U.S. Pat. No. 5,980,886.

The vector encoding urokinase can be any type of vector suitable for delivery to the rat and capable of expressing the urokinase gene. Such vectors include viral vectors or plasmid vectors. In one embodiment, the vector is an adenovirus vector. In another embodiment, the vector is an AAV vector. The vector encoding urokinase can be administered by any suitable means known in the art. In one embodiment, the vector is administered intravenously. In one aspect, the vector is administered by retroorbital injection. The vector encoding urokinase can be administered any time prior to injection of the heterologous hepatocytes. Typically, the vector is administered to allow sufficient time for urokinase to be expressed. In one embodiment, the vector is administered 24 to 48 hours prior to hepatocyte injection.

The length of time for hepatocyte expansion can vary and will depend on a variety of factors, including the number of hepatocytes originally transplanted, the number of heterologous hepatocytes desired following expansion and/or the desired degree of liver repopulation with the heterologous hepatocytes. In some cases, these factors will be dictated by the desired use of the hepatocytes or the desired use of the rat engrafted with the heterologous hepatocytes. In some embodiments, the heterologous hepatocytes are expanded in the rat for at least about 3 days, at least about 5 days, at least about 7 days, at least about 2 weeks, or at least about 4 weeks, at least about 5 weeks, at least about 6 weeks, at least about 2 months, at least about 3 months, at least about 4 months, at least about 5 months, at least about 6 months, at least about 7 months, at least about 8 months, at least about 9 months, at least about 10 months or at least about 11 months. In particular examples, the heterologous hepatocytes are expanded in the rat for at least 7 days. In other examples, the heterologous hepatocytes are expanded in the rat for at least 6 months. In some examples, the heterologous hepatocytes are expanded in the rat no more than 12 months.

In some embodiments, the rats with a hepatic deficiency can be administered an agent that inhibits, delays, avoids or prevents the development of liver disease in the rat. Administration of such an agent avoids liver dysfunction and/or death of the rat prior to repopulation of the rat with healthy (e.g., FAH-expressing) hepatocytes. The agent can be any compound or composition known in the art to inhibit liver disease. One such agent is 2-(2-nitro-4-trifluoro-methyl-benzoyl)-1,3 cyclohexanedione (NTBC), but other pharmacologic inhibitors of phenylpyruvate dioxygenase, such as methyl-NTBC can be used. NTBC (or another compound with a liver protective effect) is administered to regulate the development of liver disease in the Fah-deficient rat. The dose, dosing schedule and method of administration can be adjusted as needed to avoid liver dysfunction in the Fah-deficient rat. In some embodiments, the Fah-deficient rat is further administered NTBC for at least two days, at least three days, at least four days, at least five days or at least six days following hepatocyte transplantation. In some embodiments, the Fah-deficient rat is further administered NTBC for at least about one week, at least about two weeks, at least about three weeks, at least about four weeks, at least about one month, at least about two months, at least about three months, at least about four months, at least about five months, or at least about six months. In some embodiments, the NTBC (or another compound with a liver protective effect) is withdrawn at about two days, about three days, about four days, about five days, about six days or about seven days following hepatocyte transplantation.

The dose of NTBC administered to the Fah-deficient rat can vary. In some embodiments, the dose is about 0.5 mg/kg to about 30 mg/kg per day, preferably from about 1 mg/kg to about 25 mg/kg, more preferably from about 10 mg/kg per day to about 20 mg/kg per day, and even more preferably about 20 mg/kg per day. NTBC can be administered by any suitable means, such as, but not limited to, in the drinking water, in the food or by injection. In one embodiment, the concentration of NTBC administered in the drinking water is about 1 to about 30 mg/L, preferably from about 10 to about 25 mg/L, more preferably from about 15 to about 20 mg/L, and even more preferably about 20 mg/L.

In some embodiments, the method further includes collecting the expanded heterologous hepatocytes from the rat. Further provided is an expanded heterologous hepatocyte isolated from the liver of the rat.

Further provided herein is a method of serial transplantation of heterologous hepatocytes (or hepatocytes from another species) in the recipient rat. The method comprises collecting the expanded heterologous hepatocytes from a first recipient rat and further expanding the hepatocytes in a second, third, fourth or additional recipient rat. The expanded hepatocytes can be collected from the rat using any one of a number of techniques. For example, the hepatocytes can be collected by enzymatic digestion of the rat liver, followed by gentle mincing, filtration, and centrifugation. Furthermore, the hepatocytes can be separated from other cell types, tissue and/or debris using well-known methods, such as by using an antibody that specifically recognizes the cell type of the engrafted hepatocyte species. Such antibodies include, but are not limited to an antibody that specifically binds to a class I major histocompatibility antigen, such as anti-human HLA-A,B,C (Markus et al. *Cell Transplantation* 6:455-462, 1997). Antibody bound hepatocytes can then be separated by panning (which utilizes a monoclonal antibody attached to a solid matrix), fluorescence activated cell sorting (FACS), magnetic bead separation or the like. Alternative methods of collecting hepatocytes are well known in the art.

Further provided is a method of assessing the effect of an exogenous agent (xenobiotic) on hepatocytes, such as human hepatocytes, in vivo. In some embodiments, the method includes administering the exogenous agent to a rat model described herein which has been transplanted with heterologous hepatocytes and measuring at least one marker of liver function in the rat. In some embodiments, the at least one marker of liver function is selected from AST, ALT, bilirubin, alkaline phosphatase and albumin, and wherein an increase in AST, ALT, bilirubin or alkaline phosphatase, or a decrease in albumin in the rat relative to the rat prior to administration of the exogenous agent, indicates the exogenous agent is toxic. In some embodiments, the exogenous agent is a known or suspected toxin.

III. Animal Models and Uses Thereof

According to one embodiment described herein is a method for generation of Fah-deficient rats by homologous recombination using an AAV targeting construct in rat embryonic stem (ES) cells. The examples describe the generation of an AAV targeting construct containing a neomycin-resistance cassette and 5' and 3' homology arms that target the construct for insertion in exon 3 of the rat Fah gene. Rat ES cells were infected with the AAV targeting vector and selected for neomycin resistance to isolate individual cell clones with integrated vector. The FAH knockout (KO) ES cells can be injected into rat blastocysts and transferred to E3.5 pseudo-pregnant SD rats. The progeny from these rats can be genotyped and chimeric rats can be bred to generate heterozygote males and females that can be bred to generate homozygote FAH KO rats. This disclosure is not limited to one particular method of generating an Fah-deficient rat, but encompasses any method known in the art to produce an Fah-deficient rat, including, without limitation, TALEN, zinc finger nucleases, meganucleases, SCNT, and the like.

In one or more embodiments, additional metabolic enzymes in the tyrosine catabolic pathway can be targeted in addition to or in lieu of Fah to generate animal models with severe liver dysfunction ("hepatic deficiency"). For example, genes encoding for tyrosine aminotransferase, 4-hydroxy-phenylpyruvate dioxygenase, homogentisate 1,2-dioxygenase, and/or maleylacetoacetate isomerase can be targeted for disruption using methods similar to those described herein. In the absence of treatment, rats deficient (i.e., have decreased expression, activity, or function) in one or more of the above enzymes will develop a liver dysfunction such as tyrosinemia (I, II, III), hawkinsinuria, alkaptonuria, and the like, which ultimately results in death of endogenous hepatocytes. Thus, as with Fah-deficient models, such rats can also be repopulated with hepatocytes from other species, including humans.

Also disclosed herein is the engraftment of heterologous hepatocytes in livers of immunodeficient rats. Accordingly, the use of immunodeficient rats (in the absence of Fah-deficiency) is contemplated herein for expansion of heterologous hepatocytes. Humanized rats (i.e. rats having livers reconstituted with human hepatocytes) can also be used, for example, as a source of hepatocytes for human liver reconstitution as well as for pharmacology, toxicology, and gene therapy studies, as discussed below.

In some cases, prior to transplantation with heterologous hepatocytes, acute liver damage will be induced in the rats using any suitable model of liver injury including uPa, TK, selective embolism, transient ischemia, retrorsine, monocrotoline, irradiation with gamma rays, carbon tetrachloride, and the like. In some embodiments liver damage is induced by administering a recombinant adenovirus expressing the urokinase plasminogen-like enzyme. After administration of urokinase (such as 24 hours later), the heterologous hepatocytes can be delivered via intra-splenic injection where the hepatocytes will travel through the vasculature to reach the liver. In addition, immune suppression drugs can optionally be given to the rats before, during and after the transplant to eliminate the host versus graft response in the rat from the xenografted heterologous hepatocytes. By cycling the rats off NTBC for defined periods of time, the rat cells become quiescent and the engrafted cells will have a proliferative advantage leading to replacement of endogenous rat hepatocytes with heterologous hepatocytes. In the case of human hepatocytes, this generates rats with high levels of humanized livers. Heterologous hepatocyte repopulation levels can be determined through quantitation of human serum albumin levels correlated with immunohistochemistry of liver sections from transplanted rats.

A. Expansion of Hepatocytes and their Medical Use

The present disclosure contemplates the use of heterologous hepatocytes expanded in and collected from a recipient rat as a source of hepatocytes for liver reconstitution in a subject in need of such therapy. Reconstitution of liver tissue in a patient by the introduction of hepatocytes is a potential therapeutic option for patients with acute liver failure, either as a temporary treatment in anticipation of liver transplant or as a definitive treatment for patients with isolated metabolic deficiencies (Bumgardner et al. *Transplantation* 65: 53-61, 1998). Hepatocyte reconstitution may be used, for example, to introduce genetically modified hepatocytes for gene therapy or to replace hepatocytes lost as a result of disease, physical or chemical injury, or malignancy (U.S. Pat. No. 6,995,299). For example, use of transfected hepatocytes in gene therapy of a patient suffering from familial hypercholesterolemia has been reported (Grossman et al. *Nat. Genet.* 6: 335, 1994). In addition, expanded human hepatocytes can be used to populate artificial liver assist devices. Particular methods of transplanting and expanding heterologous hepatocytes in rats, as well medical uses of the expanded heterologous hepatocytes, are described in greater detail below.

1. Pre-Immune Fetal Transplantation of Hepatocytes

One method disclosed herein for expanding heterologous hepatocytes in the rats includes transplanting heterologous hepatocytes and/or hepatocyte progenitors into fetuses. In one or more embodiments, the disclosed method for pre-immune hepatocyte transplantation in rats includes breeding Fah-deficient rats to each other to generate only homozygous Fah-knockout offspring. At approximately day 9-15 of gestation (e.g., day 12), the Fah-deficient rat fetus is surgically externalized and injected with heterologous hepatocytes via the umbilical vein or directly into the fetal liver. This method would also work with genetically modified immunodeficient rat fetuses, or rat fetuses having another hepatic deficiency.

The number of heterologous hepatocytes injected into the rat can vary and will depend on the desired use, route of delivery and other factors. In some embodiments, the fetus is injected with from about 50,000 to about $1 \times 10^8$, such as about 500,000 to about $1 \times 10^7$, heterologous hepatocytes. In some examples, the fetus is injected with about $1 \times 10^6$ to about $1 \times 10^8$, such as about $1 \times 10^7$, heterologous hepatocytes. In one non-limiting example, the fetus is injected with approximately $1 \times 10^7$ heterologous hepatocytes directly into the fetal liver. In other examples, the number of heterologous hepatocytes injected is about 100,000 to about 500,000, such as about 300,000. Because of the immature nature of the immune system during fetal development, the fetus will develop immunological tolerance to heterologous hepatocytes. Thus, it is not necessary to treat a rat that has been transplanted with heterologous hepatocytes during fetal development with immunosuppressive agents.

In one or more embodiments, the pregnant rat is maintained on an effective amount of a pharmacologic inhibitor of phenylpyruvate dioxygenase, such as NTBC or another compound, to avoid liver dysfunction or failure in the Fah-deficient fetus throughout pregnancy. The dose of pharmacologic inhibitor of phenylpyruvate dioxygenase can vary. Exemplary dosages are discussed above. The dose of NTBC can be modified as needed to avoid liver dysfunction in the Fah-deficient rats. After birth, the Fah-deficient rat engrafted with heterologous hepatocytes will no longer be administered NTBC to permit expansion of the heterologous hepatocytes. In some examples, the Fah-deficient rat will no longer be administered NTBC from immediately after birth. In other examples, the dose of NTBC is gradually reduced over time, such as over about 1 to 6 days, such as 1 to 6 days from the date of birth.

2. Post-Natal Transplantation of Hepatocytes

A second method of expanding heterologous hepatocytes in rat models described herein includes post-natal transplantation of the heterologous hepatocytes and/or hepatocyte progenitors into the rats. In some embodiments, the rats are transplanted shortly after birth, such as within 2 days or within a week of birth. In other embodiments, older rats, including adult rats, are transplanted. The heterologous hepatocytes are generally transplanted via the hepatic artery, intrasplenic injection or portal vein. In some embodiments, the Fah-deficient rats are maintained on a pharmacologic inhibitor of phenylpyruvate dioxygenase, such as NTBC or methyl-NTBC, to inhibit or avoid liver dysfunction. Prior to transplantation of the heterologous hepatocytes, the rats can be treated with one or more immunosuppressive agents to prevent rejection of the heterologous hepatocytes. Typically, the one or more immunosuppressive agents are administered about two days prior to heterologous hepatocyte transplantation; however, the timing for initiating treatment with the immunosuppressive agents can vary if necessary in order to achieve optimal results. Administration of the immunosuppressive agents will typically continue indefinitely in an amount effective to avoid rejection of the heterologous hepatocytes.

Once transplantation of the heterologous hepatocytes has been completed, the Fah-deficient rats are no longer administered NTBC to allow for expansion of the heterologous hepatocytes. The presence of the heterologous hepatocytes (which are not deficient for Fah) allows the rats to remain healthy in the absence of NTBC. In some cases, treatment with NTBC is stopped immediately after hepatocyte transplantation. In other cases, NTBC is gradually reduced over time, such as over about one to about six days. In some embodiments, the dose of NTBC when administered to the Fah-deficient rats, is about 0.2 mg/kg to about 2.0 mg/kg per day. In some examples, the dose of NTBC is about 1.0 mg/kg per day. The dose of NTBC can be modified as needed to avoid liver dysfunction in the Fah-deficient rats.

B. Sources of Heterologous Hepatocytes

Any suitable source of heterologous hepatocytes or hepatocyte precursors/progenitors can be used in the disclosed methods for transplantation in rats. For example, human hepatocytes can be derived from cadaveric donors or liver resections from various species of mammals, or can be obtained from commercial sources. Human hepatocytes can also be obtained from previously engrafted animals (i.e., humanized animals whose livers have been previously repopulated with human hepatocytes, such as the humanized FRG KO mice disclosed in WO 2008/151283 and WO 2010/127275). Methods of isolating human hepatocytes from such animals are described herein. It is anticipated that it will be possible to transplant rats with heterologous hepatocytes from donors of all ages or with cryopreserved hepatocytes. There is often a delay (typically 1 to 2 days) between isolation of human hepatocytes and transplantation, which can result in poor viability of the hepatocytes. However, the rat systems described herein can serve as a means of expanding human hepatocytes even when the number of hepatocytes is limited in number.

Methods of isolating hepatocytes are well known in the art. For example, methods of isolating hepatocytes from organ donors or liver resections are described in WO 2004/009766 and WO 2005/028640 and U.S. Pat. Nos. 6,995,299 and 6,509,514. Hepatocytes can be obtained from a liver biopsy taken percutaneously or via abdominal surgery. Heterologous hepatocytes for transplantation into a recipient rat can be isolated from mammalian liver tissue by any convenient method known in the art. Liver tissue can be dissociated mechanically or enzymatically to provide a suspension of single cells, or fragments of intact hepatic tissue may be used. For example, the hepatocytes can be isolated from donor tissue by routine collagenase perfusion (Ryan et al. *Meth. Cell Biol.* 13:29, 1976) followed by low-speed centrifugation. Hepatocytes can be further purified by filtering through a stainless steel mesh, followed by density-gradient centrifugation. Alternatively, other methods for enriching for hepatocytes can be used, such as, for example, fluorescence activated cell sorting, panning, magnetic bead separation, elutriation within a centrifugal field, or any other method well known in the art. Similar hepatocyte isolation methods can be used to collect expanded heterologous hepatocytes from a recipient rat liver.

Alternatively, heterologous hepatocytes can be prepared using the technique described by Guguen-Guillouzo et al. (*Cell Biol. Int. Rep.* 6:625-628, 1982). Briefly, a liver or portion thereof is isolated and a cannula is introduced into the portal vein or a portal branch. The liver tissue is then perfused, via the cannula, with a calcium-free buffer followed by an enzymatic solution containing collagenase (such as about 0.025% collagenase) in calcium chloride solution (such as about 0.075% calcium chloride) in HEPES buffer at a flow rate of between 30 and 70 milliliters per minute at 37° C. The perfused liver tissue is minced into small (such as about 1 cubic millimeter) pieces. The enzymatic digestion is continued in the same buffer as described above for about 10-20 minutes with gentle stirring at 37° C. to produce a cell suspension, and the released hepatocytes are collected by filtering the cell suspension through a 60-80 micrometer nylon mesh. The collected hepatocytes can then be washed in cold HEPES buffer at pH 7.0 using slow centrifugation to remove collagenase and cell debris. Non-parenchymal cells may be removed by metrizamide gradient centrifugation (see U.S. Pat. No. 6,995,299).

Hepatocytes can be obtained from fresh tissue (such as tissue obtained within hours of death) or freshly frozen tissue (such as fresh tissue frozen and maintained at or below about 0° C.). For some applications, it is preferred that the heterologous tissue has no detectable pathogens, is normal in morphology and histology, and is essentially disease-free. The hepatocytes used for engraftment can be recently isolated, such as within a few hours, or can be transplanted after longer periods of time if the cells are maintained in appropriate storage media. One such media is VIASPAN™ (a universal aortic flush and cold storage solution for the preservation of intra-abdominal organs; also referred to as University of Wisconsin solution, or UW). Hepatocytes also can be cryopreserved prior to transplantation. Methods of cryopreserving hepatocytes are well known in the art and are described, for example, in U.S. Pat. No. 6,136,525.

In addition to obtaining heterologous hepatocytes from organ donors or liver resections, the cells used for engraftment can be mammalian stem cells, such as human stem cells, or hepatocyte precursor cells that, following transplantation into the recipient rat, develop or differentiate into hepatocytes capable of expansion. Human cells with ES cell properties have been isolated from the inner blastocyst cell mass (Thomson et al., *Science* 282:1145-1147, 1998) and developing germ cells (Shamblott et al., *Proc. Natl. Acad. Sci. USA* 95:13726-13731, 1998), and human embryonic stem cells have been produced (see U.S. Pat. No. 6,200,806). As disclosed in U.S. Pat. No. 6,200,806, ES cells can be produced from human and non-human primates. Induced pluripotent stem (iPS) cells induced from human and non-human primate cells can also be obtained (see, for example, Yu et al., *Science* 318(5858):1917-1920, 2007; Takahashi et al., *Cell* 131(5):861-872, 2007; Liu et al., *Cell Stem Cell* 3(6):587-590, 2008). Generally, primate ES cells are isolated on a confluent layer of murine embryonic fibroblast in the presence of ES cell medium. ES cell medium generally consists of 80% Dulbecco's modified Eagle's medium (DMEM; no pyruvate, high glucose formulation, Gibco BRL), with 20% fetal bovine serum (FBS; Hyclone), 0.1 mM β-mercaptoethanol (Sigma), and 1% non-essential amino acid stock (Gibco BRL). Distinguishing features of ES cells, as compared to the committed "multipotential" stem cells present in adults, include the capacity of ES cells to maintain an undifferentiated state indefinitely in culture, and the potential that ES cells have to develop into every different cell type. Human ES (hES) cells express SSEA-4, a glycolipid cell surface antigen recognized by a specific monoclonal antibody (see, for example, Amit et al., *Devel. Biol.* 227:271-278, 2000). In one or more embodiments, the hepatocytes can also be from a source other than ESCs.

Human hepatocytes derived from human mesenchymal stem cells (hMSCs) can also be used in the methods described herein. Sequential exposure of bone marrow-derived hMSCs to hepatogenic factors results in differentiation of the stem cells to cells with hepatocyte properties (see Snykers et al. *BMC Dev Biol.* 7:24, 2007; Aurich et al. *Gut.* 56(3):405-15, 2007). Hepatogenic differentiation of bone marrow-derived mesenchymal stem cells and adipose tissue-derived stem cells (ADSCs) has also been described (see Talens-Visconti et al. *World J Gastroenterol.* 12(36): 5834-45, 2006). Human hepatocytes can also be generated from monocytes. Ruhnke et al. (*Transplantation* 79(9): 1097-103, 2005) describe the generation of hepatocyte-like (NeoHep) cells from terminally differentiated peripheral blood monocytes. The NeoHep cells resemble primary human hepatocytes with respect to morphology, expression of hepatocyte markers, various secretory and metabolic functions and drug detoxification activities. In addition, human hepatocytes derived from amniocytes, also can be used in the methods described herein.

Hepatocytes can also be derived by reprogramming of distinct cell types such as skin fibroblasts (Huang et al., *Nature* 475(73560:386-389, 2011).

Human ES cell lines exist and can be used in the methods disclosed herein. Human ES cells can also be derived from preimplantation embryos from in vitro fertilized (IVF) embryos. Experiments on unused human IVF-produced embryos are allowed in many countries, such as Singapore and the United Kingdom, if the embryos are less than 14 days old. Only high quality embryos are suitable for ES cell isolation. Culture conditions for culturing the one cell human embryo to the expanded blastocyst have been described (see, for example, Bongso et al., *Hum Reprod.* 4:706-713, 1989). Co-culturing of human embryos with human oviductal cells results in the production of high blastocyst quality. IVF-derived expanded human blastocysts grown in cellular co-culture, or in improved defined medium, allows isolation of human ES cells (see U.S. Pat. No. 6,200,806).

C. Collecting Heterologous Hepatocytes from Engrafted Rats

Expanded hepatocytes can be collected from recipient rats using any of a number of techniques known in the art. For example, rats can be anesthetized and the portal vein or inferior vena cava cannulated with a catheter. The liver can then be perfused with an appropriate buffer (such as a calcium- and magnesium-free EBSS supplemented with 0.5 mM EGTA and 10 mM HEPES), followed by collagenase treatment (for example, using a solution of EBSS with calcium and magnesium supplemented with 1 mg/ml collagenase II). The digested liver is removed from the animals, minced to dissociate cellular aggregates and generate a homogenous slurry. To enrich for hepatocytes the cell slurry is passed through nylon mesh (such as sequentially through 100 μm, 70 μm and 40 μm nylon mesh), followed by low speed centrifugation and washing of the cells.

Heterologous hepatocytes collected from recipient rats can be separated from rat cells or other contaminants (such as tissue or cellular debris) using any technique well known in the art. For example, such methods include using an antibody that selectively binds to the heterologous hepatocyte species. For human hepatocytes, such antibodies include, but are not limited to an antibody that specifically binds to a class I major histocompatibility antigen, such as anti-human HLA-A,B,C (Markus et al. *Cell Transplantation* 6:455-462, 1997) or CD46. Antibodies specific for human cells or human hepatocytes can be used in a variety of different techniques, including fluorescence activated cell sorting (FACS), panning or magnetic bead separation. Alternatively, antibodies which bind selectively to the rat cells can be used to remove contaminating animal cells and thereby enrich human hepatocytes. FACS employs a plurality of color channels, low angle and obtuse light-scattering detection channels, and impedance channels, among other more sophisticated levels of detection, to separate or sort cells (see U.S. Pat. No. 5,061,620) bound by the antibody. Magnetic separation involves the use of paramagnetic particles which are: 1) conjugated to the human-specific antibodies; 2) conjugated to detection antibodies which are able to bind to the human-specific antibodies; or 3) conjugated to avidin which can bind to biotinylated antibodies. Panning involves a monoclonal antibody attached to a solid matrix, such as agarose beads, polystyrene beads, hollow fiber membranes or plastic petri dishes. Cells that are bound by the antibody can be isolated from a sample by simply physically separating the solid support from the sample.

Hepatocytes collected from rats can be, for example, cryopreserved for later use, or plated in tissue culture for shipping and future use.

D. Liver Reconstitution

The rats described herein provide a system for propagating hepatocytes that can be used to reconstitute a liver, as an alternative or adjunct to a liver transplant in a human or non-human mammal. Currently, patients suffering from liver disease may have to wait for long periods of time before a suitable organ for transplant becomes available. After transplant, patients need to be treated with immunosuppressive agents for the duration of their lives in order to avoid rejection of the donor's liver. A method for propagating the patient's own remaining healthy liver cells could provide a source of functional liver tissue which would not require immunosuppression to remain viable. Accordingly, the rats disclosed herein can be used to reconstitute the liver cells of both humans and non-human mammals with liver disease and/or liver failure using their own hepatocytes, including those produced from patient specific stem cells, that have been expanded in the rats, or hepatocytes from a donor.

Reconstitution of liver tissue in a patient by the introduction of hepatocytes (also referred to as "hepatocyte transplantation") is a potential therapeutic option for patients with acute liver failure, either as a temporary treatment in anticipation of liver transplant or as a definitive treatment for patients with isolated metabolic deficiencies (Bumgardner et al., *Transplantation* 65: 53-61, 1998). A major obstacle to achieving therapeutic liver reconstitution is immune rejection of transplanted hepatocytes by the host, a phenomenon referred to (where the host and donor cells are genetically and phenotypically different) as "allograft rejection." Immunosuppressive agents have been only partially successful in preventing allograft rejection (Javregui et al., *Cell Transplantation* 5: 353-367, 1996; Makowka et al., *Transplantation* 42: 537-541, 1986).

Heterologous hepatocytes expanded in rats may also be used for gene therapy applications. In the broadest sense, such hepatocytes are transplanted into a host to correct a genetic defect. The passaged hepatocytes need not, but can be derived originally from the same individual or subject who is to be the recipient of the transplant.

In some embodiments, heterologous hepatocytes expanded in rats may be used to reconstitute liver tissue in a subject as a prelude or an alternative to liver transplant. As one non-limiting example, a subject suffering from progressive degeneration of the liver, for example, as a result of alcoholism, may serve as a donor of hepatocytes that are then expanded in a rat. The number of hepatocytes is expanded relative to the number originally obtained from the subject and transplanted into the rat. Following expansion, the expanded hepatocytes can be isolated from the rat, and can be used to reconstitute the subject's liver function. Expanding hepatocytes in rats may be used not only to increase the number of hepatocytes, but also to selectively remove hepatocytes that are afflicted with infectious or malignant disease. Specifically, a subject may be suffering from hepatitis, where some but not all of the hepatocytes are infected and infected hepatocytes can be identified by the presence of viral antigens in or on the cell surface. In such an instance, hepatocytes can be collected from the subject, and non-infected cells can be selected for expanding in one or more rats, for example by FACS. Meanwhile, aggressive steps could be taken to eliminate infection in the patient. Following treatment, the subject's liver tissue may be reconstituted by hepatocytes expanded in the one or more rats. An analogous method could be used to selectively passage non-malignant cells from a patient suffering from a liver malignancy, such as HCC.

E. Models of HT1

Hereditary tyrosinemia type 1 (HT1) is a severe autosomal recessive metabolic disease that affects the liver and kidneys. HT1 results from defects in the Fah gene, located in q23-q25 of chromosome 15 in humans and in chromosome 7 in mice. HT1 patients display a variety of clinical symptoms, such as liver damage from infancy that advances to cirrhosis; reduced coagulation factors; hypoglycemia; high concentrations of methionine, phenylalanine, and aminolevulinic acid in serum plasma; high risk of hepatocellular carcinoma; and tubular and glomerular renal dysfunction. In its severe form, a pattern of progressive liver damage begins from early infancy. In its mild form, chronic liver damage with a high incidence of hepatoma is characteristic.

Animals homozygous for Fah gene disruption have a neonatal lethal phenotype caused by liver dysfunction. It has previously been demonstrated that treatment of Fah-deficient mice with NTBC restores liver function and abolishes neonatal lethality (Grompe et al., *Nat Genet* 10:453-460, 1995). The prolonged lifespan of these animals resulted in a phenotype analogous to HT1 in humans, including the development of hepatocellular carcinoma and fibrosis. Accordingly, the Fah-deficient rats disclosed herein also represent animal models of the human disease HT1.

F. Liver Disease Model

As discussed above, Fah deficiency in rats leads to a disease phenotype similar to the human disease HT1. To prevent lethality, Fah-deficient rats are maintained on NTBC or another compound that avoids liver dysfunction, however, titration of the dose of NTBC can be used promote the development of HT1-type phenotypes, including HCC, fibrosis and cirrhosis. Accordingly, the rats with various hepatic deficiencies disclosed herein can be used to study a variety of liver diseases, including HCC and cirrhosis.

In some embodiments, the rats with humanized livers are used as animal models of human liver disease. The rats may be used as models of liver disease resulting from, for example, exposure to a toxin, infectious disease or malignancy or a genetic defect (i.e., Fah-deficiency leading to HT1). Examples of human genetic liver diseases for which the rats may serve as a model include, but are not limited to, hypercholesterolemia, hypertriglyceridemia, hyperoxaluria, phenylketonuria, maple syrup urine disease, glycogen storages diseases, lysosomal storage diseases (such as Gaucher's disease), and any inborn error of metabolism. The disclosed model systems can be used to gain a better understanding of particular liver diseases and to identify agents which may prevent, retard or reverse the disease processes.

Where the rat is to be used as a model for liver disease caused by a toxin, the Fah-deficient rat is maintained on a dosage of NTBC (or a drug having a liver protective effect similar to NTBC) effective to inhibit liver dysfunction or liver failure. The amount of toxic agent required to produce results most closely mimicking the corresponding human condition may be determined by using a number of rats exposed to incremental doses of the toxic agent. Examples of toxic agents include, but are not limited to, ethanol, acetaminophen, phenytoin, methyldopa, isoniazid, carbon tetrachloride, yellow phosphorous and phalloidin. In some cases, the rats, in the absence of human hepatocytes, are used as the model for evaluating the effect of a toxin. In other examples, the rat is transplanted with human hepatocytes to evaluate the effect of the toxin on human hepatocytes. In these examples, it is not necessary to maintain the Fah-deficient rat on a dosage of a liver protective drug such as NTBC to preserve liver function. Typically, expansion of human hepatocytes is allowed to proceed to the point where the size of the human hepatocyte population is substantial (e.g. has approached a maximum), before the rat is exposed to the toxic agent.

In embodiments where a rat is to be used as a model for malignant liver disease (such as HCC or hepatoma), the Fah-deficient rat is administered a high enough dose of a liver protective drug such as NTBC to prevent fatality due to liver dysfunction, but low enough to allow the development of HCC or other liver malignancy. Alternatively, the Fah-deficient rat can be maintained on a dose of the drug that preserves liver function and the malignancy can be produced by exposure to a transforming agent or by the introduction of malignant cells. In some examples, the rat, in the absence of heterologous hepatocytes, is used as the model for malignant liver disease. In other examples, the rat is transplanted with human hepatocytes to evaluate malignant liver disease of the human cells. In these examples, it is not necessary to maintain the Fah-deficient rats on the liver protective drug, such as NTBC. The transforming agent or malignant cells may be introduced with the initial colonizing introduction of human hepatocytes or after the human hepatocytes have begun to proliferate in the host rat. In the case of a transforming agent, it may be preferable to administer the agent at a time when heterologous hepatocytes are actively proliferating. Examples of transforming agents include aflatoxin, dimethylnitrosamine, and a choline-deficient diet containing 0.05-0.1% w/w DL-ethionine (Farber and Sarma, 1987, in Concepts and Theories in Carcinogenesis, Maskens et al., eds, Elsevier, Amsterdam, pp. 185-220). Such transforming agents may be administered either systemically to the rat or locally into the liver itself. Malignant cells may be inoculated directly into the liver.

G. Model for Hepatic Infections

Hepatocytes expanded in and collected from recipient rats can also be used for a variety of microbiological studies. A number of pathogens (e.g., bacteria, viruses and parasites) will only replicate in a human host or in primary human hepatocytes. Thus, having a sufficient source of primary human hepatocytes is critical for studies of these pathogens. The expanded human hepatocytes can be used for studies of viral infection and replication or for studies to identify compounds that modulate infection of hepatic viruses. Methods for using primary human hepatocytes in studies of hepatic viruses are described in, for example, European Patent No. 1552740, U.S. Pat. No. 6,509,514 and PCT Publication No. WO 00/17338. Examples of hepatic viruses include hepatitis A virus, hepatitis B virus (HBV), hepatitis C virus (HCV) and cytomegalovirus (CMV). Examples of parasites that infect the liver include, for example, the causative agents of malaria (*Plasmodium* species, including *Plasmodium falciparum, Plasmodium vivax, Plasmodium ovale, Plasmodium malariae* and *Plasmodium knowlesi*) and the causative agents of leishmaniasis (*Leishmania* species, including *L. donovani, L. infantum, L. chagasi, L. mexicana, L. amazonensis, L. venezuelensis, L. tropica; L. major; L. aethiopica, L. (V.) braziliensis, L. (V.) guyanensis, L. (V.) panamensis*, and *L. (V.) peruviana*).

In addition to using the human hepatocytes expanded in rats for microbiological studies, the rats themselves can serve as animal models of hepatic pathogen infection. For example, rats repopulated with human hepatocytes can be infected with a hepatic pathogen and used to screen candidate agents for treatment of the infection. Candidate agents include any compound from any one of a number of chemical classes, such as small organic compounds. Candidate agents also include biomolecules, such as, for example, nucleic acid molecules (including antisense oligonucleotides, small interfering RNAs, microRNAs, ribozymes, short hairpin RNAs, expression vectors and the like), peptides and antibodies, saccharides, fatty acids, steroids, purines, pyrimidines, derivatives, structural analogs or combinations thereof.

Candidate agents can be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Using rats to study HCV and HBV infection, as well as evaluate candidate agents for the treatment of these infections, is discussed below. However, the methods can be applied to any hepatic pathogen of interest. In one embodiment, a rat is used to identify agents that inhibit viral infection, decrease viral replication, and/or ameliorate one or more symptoms caused by HBV or HCV infection. In general, the candidate agent is administered to the rat, and the effects of the candidate agent assessed relative to a control. For example, the candidate agent can be administered to an HCV-infected rat model, and the viral titer of the treated rat (e.g., as measured by RT-PCR of serum samples) can be compared to the viral titer of the rat prior to treatment and/or to an untreated HCV-infected rat. A detectable decrease in viral titer of an infected rat following treatment with a candidate agent is indicative of antiviral activity of the agent.

The candidate agent can be administered in any suitable manner appropriate for delivery of the agent. For example, the candidate agent can be administered by injection (such as by injection intravenously, intramuscularly, subcutaneously, or directly into the target tissue), orally, or by any other desirable means. In some cases, the in vivo screen will involve a number of rats receiving varying amounts and concentrations of the candidate agent (from no agent to an amount of agent that approaches an upper limit of the amount that can be safely delivered to the animal), and may include delivery of the agent in different formulations and routes. Candidate agents can be administered singly or in combinations of two or more, especially where administration of a combination of agents may result in a synergistic effect.

The activity of the candidate agent can be assessed using any one of a variety of means known in the art. For example, where the rat is infected with a hepatotropic pathogen (e.g., HBV or HCV), the effect of the agent can be assessed by examining serum samples for the presence of the pathogen (e.g., measuring viral titer) or markers associated with the presence of the pathogen (e.g., a pathogen-specific protein or encoding nucleic acid). Qualitative and quantitative methods for detecting and assessing the presence and severity of viral infection are well known in the art. In one embodiment, the activity of an agent against HBV infection can be assessed by examining serum samples and/or tissue sections for the presence of a viral antigen (such as HBV surface antigen (HBsAg) or HBV core antigen (HbcAg)). In another embodiment, the activity of an agent against viral infection can be assessed by examining serum samples for the presence of viral nucleic acid (such as HCV RNA). For example, HCV RNA can be detected using, for example, reverse transcriptase polymerase chain reaction (RT-PCR), competitive RT-PCR or branched-DNA (bDNA) assay, detection of negative-strand RNA (the replicative intermediate of HCV) by RT-PCR, or sequencing of viral RNA to detect mutation/shift in the viral genome ("quasispecies evolution") with therapy. Alternatively or in addition, the host liver may be biopsied and in situ RT-PCR hybridization performed to demonstrate directly any qualitative or quantitative alterations in the amount of viral particles within tissue sections. Alternatively or in addition, the host can be euthanized and the liver examined histologically for signs of infection and/or toxicity caused by the agent.

The rat models described herein can also be used to screen candidate vaccines for their ability to prevent or ameliorate infection by a hepatotropic pathogen. In general, a vaccine is an agent that, following administration, facilitates the host in mounting an immune response against the target pathogen. The humoral, cellular, or humoral/cellular immune response elicited can facilitate inhibition of infection by the pathogen against which the vaccine is developed. Of particular interest in the present disclosure are vaccines that elicit an immune response that inhibits infection by and/or intrahepatic replication of a hepatotropic pathogen (e.g., a microbial, viral, or parasitic pathogen), particularly a viral pathogen, such as HBV and/or HCV.

To evaluate candidate vaccines, the rats are transplanted with human hepatocytes to repopulate the rat liver with human hepatocytes. Screening for an effective vaccine is similar to the screening methods described above. In some embodiments, the candidate vaccine is administered to the rat prior to inoculation with the hepatotropic pathogen. In some cases, the candidate vaccine is administered by providing a single bolus (e.g., intraperitoneal or intramuscular injection, topical administration, or oral administration), which is optionally followed by one or more booster immunizations. The induction of an immune response can be assessed by examining B and T cell responses that are specific for the antigen/vaccine according to methods well known in the art. The immunized rat is then challenged with the hepatotropic pathogen. Typically, several immunized rats are challenged with increasing titers of the pathogen. The rats are then observed for development of infection, and the severity of infection is assessed (such as by assessing the titer of the pathogen present, or examining human hepatocyte function parameters). Vaccine candidates that provide for a significant decrease in infection by the pathogen and/or a significant decrease in the severity of disease that results post-challenge are identified as viable vaccines.

H. Pharmacology, Toxicology and Gene Therapy Studies

The described rat models and/or heterologous hepatocytes expanded in and collected from the rats can be used to evaluate alterations in gene expression in such hepatocytes by any pharmacologic compound, such as small molecules, biologicals, environmental or biological toxins or gene delivery systems.

For example, human hepatocytes expanded in and collected from rats can be used to evaluate toxicity of particular compounds in human cells. Methods of testing toxicity of compounds in isolated hepatocytes are well known in the art and are described, for example, in PCT Publication No. WO 2007/022419. Similarly, rats transplanted with human hepatocytes can be used to evaluate the toxicity of exogenous agents. In some embodiments, the exogenous agent is a known or suspected toxin.

In some embodiments, rats transplanted with human hepatocytes (or human hepatocytes expanded in and collected from rats) are used to evaluate any one of a number of parameters of drug metabolism and pharmacokinetics. For example, studies can be carried out to evaluate drug metabolism, drug/drug interactions in vivo, drug half-life, routes of excretion/elimination, metabolites in the urine, feces, bile, blood or other bodily fluid, cytochrome p450 induction, enterohepatic recirculation, and enzyme/transporter induction.

In some embodiments, rats transplanted with heterologous hepatocytes (or heterologous hepatocytes expanded in and collected from rats) are used to evaluate toxicology and safety of a compound, including therapeutic agents or candidate agents (such as small molecules or biologicals), environmental or biological toxins, or gene delivery systems. For example, cell cycle proliferation in expanded human hepatocytes can be evaluated, such as to determine the risk of cancer following exposure to the compound. Toxicity to hepatocytes can also be assessed, such as by histology, apoptosis index, liver function tests, gene expression analysis, metabolism analysis and the like. Analysis of hepatocyte metabolism can also be performed, such as analysis of metabolites after infection of stable isotope precursors.

The efficacy of particular drugs can also be evaluated in rats transplanted with human hepatocytes. Such drugs include, for example, drugs to treat hyperlipidemia/atherosclerosis, hepatitis and malaria.

In some embodiments, rats transplanted with human hepatocytes (or human hepatocytes expanded in and collected from rats) are used to study gene therapy protocols and vectors. For example, the following parameters can be evaluated: transduction efficiency of gene delivery vehicles including viral and non-viral vectors; integration frequency and location of genetic payloads (integration site analysis); functionality of genetic payloads (gene expression levels, gene knockdown efficiency); and side effects of genetic payloads (analysis of gene expression or proteomics in human hepatocytes in vivo).

IV. Vectors Encoding Urokinase

In some embodiments of the methods described herein, the rats are administered a vector encoding urokinase prior to transplantation of heterologous hepatocytes. Ectopic expression of urokinase induces hepatocellular death and subsequently promotes liver regeneration, and can thus aid in the efficiency of hepatocyte engraftment (Lieber et al., *Proc Natl Acad Sci USA* 92:6210-6214, 1995).

In one embodiment, the urokinase (also known as urokinase plasminogen activator (uPA)) is the secreted form of human urokinase. In another embodiment, the urokinase is a modified, non-secreted form of urokinase (see U.S. Pat. No. 5,980,886). Any type of suitable vector for expression of urokinase in animals is contemplated. Such vectors include plasmid vectors or viral vectors. Suitable vectors include, but are not limited to, DNA vectors, adenovirus vectors, retroviral vectors, pseudotyped retroviral vectors, AAV vectors, gibbon ape leukemia vector, VSV-G, VL30 vectors, liposome mediated vectors, and the like. In one embodiment, the viral vector is an adenovirus vector. The adenovirus vector can be derived from any suitable adenovirus, including any adenovirus serotype (such as, but not limited to Ad2 and Ad5). Adenovirus vectors can be first, second, third and/or fourth generation adenoviral vectors or gutless adenoviral vectors. The non-viral vectors can be constituted by plasmids, phospholipids or liposomes (cationic and anionic) of different structures. In another embodiment, the viral vector is an AAV vector. The AAV vector can be any suitable AAV vector known in the art.

Viral and non-viral vectors encoding urokinase are well known in the art. For example, an adenovirus vector encoding human urokinase is described in U.S. Pat. No. 5,980,886 and by Lieber et al. (*Proc. Natl. Acad. Sci. U.S.A.* 92(13): 6210-4, 1995). U.S. Patent Application Publication No. 2005-176129 and U.S. Pat. No. 5,585,362 describe recombinant adenovirus vectors and U.S. Pat. No. 6,025,195 discloses an adenovirus vector for liver-specific expression. U.S. Patent Application Publication No. 2003-0166284 describes adeno-associated virus (AAV) vectors for liver-specific expression of a gene of interest, including urokinase. U.S. Pat. Nos. 6,521,225 and 5,589,377 describe recombinant AAV vectors. PCT Publication No. WO 0244393 describes viral and non-viral vectors comprising the human urokinase plasminogen activator gene. An expression vector capable of high level of expression of the human urokinase gene is disclosed in PCT Publication No. WO 03087393. Each of the aforementioned patents and publications are herein incorporated by reference.

Vectors encoding urokinase can optionally include expression control sequences, including appropriate promoters, enhancers, transcription terminators, a start codon (i.e., ATG) in front of a protein-encoding gene, splicing signal for introns and maintenance of the correct reading frame of that gene to permit proper translation of mRNA, and stop codons. Generally expression control sequences include a promoter, a minimal sequence sufficient to direct transcription.

The expression vector can contain an origin of replication, a promoter, as well as specific genes which allow phenotypic selection of the transformed cells (such as an antibiotic resistance cassette). Generally, the expression vector will include a promoter. The promoter can be inducible or constitutive. The promoter can be tissue specific. Suitable promoters include the thymidine kinase promoter (TK), metallothionein I, polyhedron, neuron specific enolase, thyrosine hyroxylase, beta-actin, or other promoters. In one embodiment, the promoter is a heterologous promoter.

In one example, the sequence encoding urokinase is located downstream of the desired promoter. Optionally, an enhancer element is also included, and can generally be located anywhere on the vector and still have an enhancing effect. However, the amount of increased activity will generally diminish with distance.

The vector encoding urokinase can be administered by a variety of routes, including, but not limited to, intravenously, intraperitoneally or by intravascular infusion via portal vein. The amount of vector administered varies and can be determined using routine experimentation. In one embodiment, rats are administered an adenovirus vector encoding urokinase at a dose of about $1 \times 10^8$ to about $1 \times 10^{10}$ plaque forming units, such as about $5 \times 10^9$ plaque forming units.

In one embodiment, the rat is administered an adenovirus vector encoding human urokinase. Adenovirus vectors have several advantages over other types of viral vectors, such as they can be generated to very high titers of infectious particles; they infect a great variety of cells; they efficiently transfer genes to cells that are not dividing; and they are seldom integrated in the guest genome, which avoids the risk of cellular transformation by insertional mutagenesis (Douglas and Curiel, *Science and Medicine*, March/April 1997, pages 44-53; Zern and Kresinam, *Hepatology*:25(2), 484-491, 1997). Representative adenoviral vectors which can be used to encode urokinase are described by Stratford-Perricaudet et al. (*J. Clin. Invest.* 90: 626-630, 1992); Graham and Prevec (In Methods in Molecular Biology: Gene Transfer and Expression Protocols 7: 109-128, 1991); and Barr et al. (*Gene Therapy*, 2:151-155, 1995).

Additional advantages of the described embodiments will be apparent to those skilled in the art based upon the examples.

EXAMPLES

The following examples are provided to illustrate certain particular features and/or embodiments. These examples should not be construed to limit the disclosure to the particular features or embodiments described.

Example 1

Figure 2:
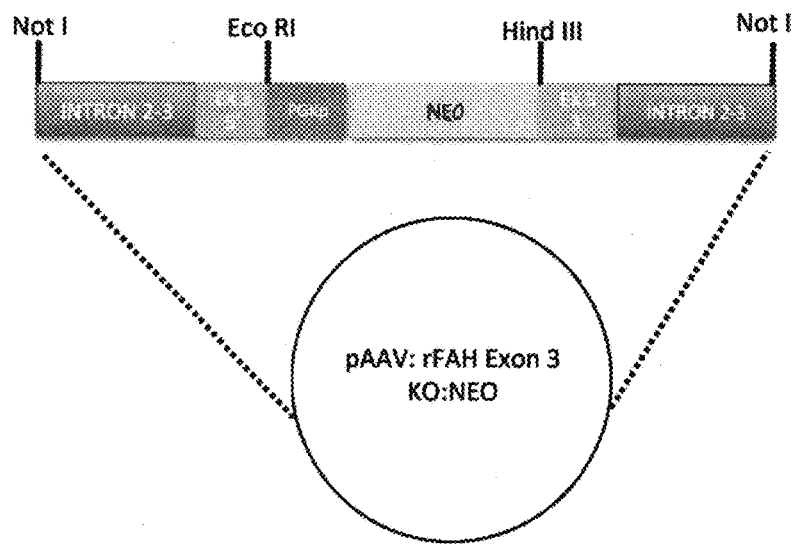
FIG. 2 is a schematic diagram showing the rat Fah targeting construct containing the 1.5 kb 5' homology region and the 1.5 kb 3' homology region flanked by the 1.7 kb selection cassette PGK:NEO.

Generation of the AAV-rFAH:PGK-NEO Null Targeting Vector and Production of FAH KO Rat ES Cells The rat FAH KO construct targets exon 3 of the FAH gene. Rat ES cell genomic DNA was used to generate 5' and 3' FAH homology regions for the targeting construct. A 5' FAH homology region was generated using a forward primer 1.5 kb upstream of exon 3 (intron 1-2; Table 1), and the reverse primer containing a stop codon ending 54 bp into exon 3 of the FAH gene (SEQ ID NO:1; FIG. 1). A 3' FAH homology region was generated using a forward primer starting 90 bp into exon3 and ending in intron 4-5 (1.5 kb; Table 1). The two 1.5 kb PCR products were cloned, sequenced and ligated to a PGK:NEO selection cassette totaling 4.7 kb (FIG. 2). The nucleotide sequence of the targeting cassette is set forth herein as SEQ ID NO:2.

The 4.7 kb fragment was ligated into the pcDNA 3.1 vector, which was linearized and transfected into rat 208D fibroblast cells to examine NEO resistance. The cells were selected with 500 μg/mL G418 for 1 week. Resistant 208D clones were obtained. The 4.7 kb cassette was then ligated into the pAAV2 shuttle vector, and clones containing the entire FAH KO cassette were selected and the recombinant AAV was generated. The AAV-rFAH:PGK-NEO construct was checked for intact internal repeat sequences and sequenced before being used for AAV production.

TABLE 1

Primers used in the design of rFAH construct

| Primer Location | Primer Sequence 5' to 3' | SEQ ID NO: |
|---|---|---|
| rFAH Intron 1-2 FOR | gtagcgaattcgcggccgcGCTGTGAGGTCAGAGACCAGCC | 3 |
| rFAH Exon 3 REV | ggatagaattcGTCACCATGCCGCTTGGCCGAGGCCC | 4 |
| rFAH Exon 3 FOR | gtagcaagctt GCCAGCCAAGCCCAGCTCAGA | 5 |
| rFAH Intron 3-4 REV | ggataggtaccgcggccgcGACCTCTAGTTCCATGTATGG | 6 |
| 5' FAH FOR genotyping | gaggccttgttcacacatga | 7 |
| 5'FAH REV genotyping | ctaaagcgcatgctccagac | 8 |
| 3' FAH FOR genotyping | attgcatcgcattgtctgag | 9 |
| 3' FAH REV genotyping | agtctcctgcagagggaaca | 10 |
| Neo genotyping FOR | TGCTCCTGCCGAGAAAGTAT | 11 |
| Neo genotyping REV | CAACAGATGGCTGGCAACTA | 12 |
| 5' FAH FOR (CAG) | gtagcgaattcgcggccgcGCTGTGAGGTCAGAGACCAGCC | 13 |
| 5' FAH REV (CAG) | tagtcgacgtcaaggatgctcttgcctcct | 14 |
| 3' FAH FOR (CAG) | gcaggtggtgccacttgtccccagttgagg | 15 |
| 3' FAH REV (CAG) | gtatgcatatcgatggaattcccctttcca | 16 |

Figure 3:
FIG. 3 is a schematic diagram of the rat Fah gene with the integrated targeting KO cassette containing the PGK:NEO sequence.
Figure 6:
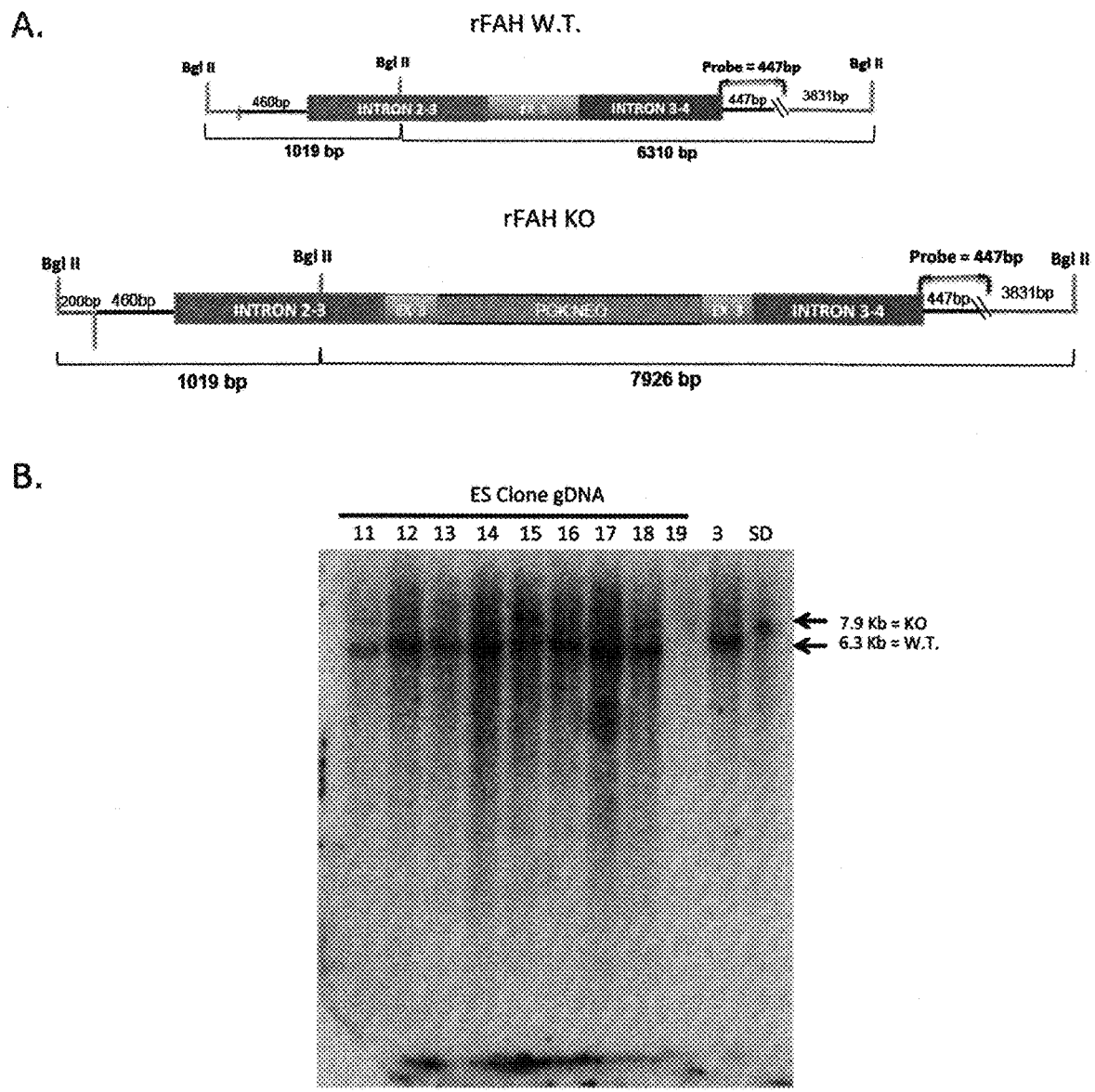
FIG. 6 shows (A) a schematic of the rFah gene WT and KO genome of the targeted region. The arrows and bracket indicate the $^{32}$P-labeled PCR product used for hybridizing the southern blot; and (B) a southern blot image. Fifteen µg of genomic DNA from each ES clones was digested with Bgl II restriction endonuclease overnight at 37° C. The digested products were electrophoresed on a 0.7% Agarose:TBE gel, the DNA was exposed to acid depurination prior to capillary transfer to nylon membrane with alkaline transfer buffer. The membrane was hybridized with $^{32}$P labeled probe from the indicated PCR product in A and B.

Purified, high titer virus was propagated and used to transduce rat embryonic stem cells. Recombinant FAH KO clones were selected using 100 μg/mL of G418. The ES cell clones that were able to grow under the selection were further amplified and genomic DNA was isolated. ES cell clones from the 95 G418 selected clones integrated into the correct locus of the rat genome as determined by PCR using FAH specific primers for the 5' end or 3' end of the integration site. Ten ES clones were further validated by Southern blot analysis to confirm correct genomic integration of the FAH KO cassette (FIG. 3). First the ES clones were thawed and expanded in duplicate wells of a 24 well plate. One well for each clone was harvested, pelleted and frozen in liquid nitrogen, and then stored at −80° C. until ready to use. Genomic DNA was isolated from the sample by lysing the cell pellet with SDS, digesting the protein and precipitating the genomic DNA (gDNA) with saturated sodium chloride and isopropanol. Approximately 20 μg of gDNA from each clone was digested with the restriction endonuclease Bgl II, and the samples were electrophoresed on a 0.7% Agarose:Tris-borate-EDTA gel for 6 hours at 45 volts. The DNA was exposed to acid depurination prior to capillary transfer with alkaline transfer buffer. The recombined FRG KO clones were identified by hybridization of the nylon membrane using a $^{32}$P labeled probe that mapped immediately to the 3' end of the FRG KO:PGK-Neomycin cassette. FIG. 4 is a schematic of the rFah gene with the integrated targeting cassette. Knock-out recombinant clones were identified by a unique 7.9 Kb fragment. The results are shown in FIGS. 5-6.

FIG. 5(a) confirms integration by homologous recombination. By using the 5' FAH+NEO (reverse) and 3' FAH+NEO (forward) primers, it was confirmed that both flanks were intact as predicted for integration into exon 3 by homologous recombination. FIG. 5(b) is the control gel confirming the presence of DNA in the samples. FIG. 6 shows a schematic of the rFah gene wild type and KO genome of the targeted region, along with the Southern Blot using an Fah probe. Both the untargeted and targeted alleles are visualized and have the expected band sizes. This confirms proper targeting of the rat Fah locus in clones 11, 15, and 18.

The targeted FAH knock-out ES cells can be used to generate an Fah KO rat using procedures reported by Tong et al. (*Nature* 467(7312):211-213, 2010).

Example 2

Generation of FAH KO Rats and Transplantation of Human Hepatocytes

FAH KO rats were generated by injecting FAH KO ES cells into rat blastocysts, which are then transferred to E3.5 pseudo-pregnant SD rats. The chimeric progeny from these rats are bred to generate heterozygous FAH KO rats by germline transmission. Male and female heterozygotes are then further bred to generate FAH knockout rats. The deletion of the FAH gene allows for the induction of liver damage to aid in high levels of engraftment and repopulation of the liver with transplanted human hepatocytes.

Prior to transplantation with human hepatocytes, acute liver damage is induced in the rats by dosing with a recombinant adenovirus expressing the plasminogen-like urokinase enzyme. Twenty-four hours later the human hepatocytes are delivered via intra-splenic injection where the hepatocytes will travel through the vasculature to reach the liver. In addition, immune suppression drugs are given to the rats before, during and after the transplant to eliminate the host versus graft response in the rat from the xenografted human hepatocytes. By cycling the rats off NTBC for defined periods of time, the rat cells become quiescent and the human cells have a proliferative advantage, leading to replacement of rat hepatocytes with human hepatocytes, and generating rats with high levels of human chimerism in the liver. Human hepatocyte repopulation levels are determined through the quantitation of human serum albumin levels and other human specific markers and correlated with immunohistochemistry of liver sections from transplanted rats.

Example 3

Generation of the Il2rg Construct

The rat Il2rg construct targets exon 3 of the Il2rg gene. Rat ES cell genomic DNA was used to generate 5' and 3' Il2rg homology regions for the targeting construct. A 5' Il2rg homology region was generated using a forward primer 1.46 kb upstream of exon 3 (Table 2), and a reverse primer containing a stop codon ending 40 bp inside exon 3 of the IL2rg gene. A 3' Il2rg homology region was generated using a forward primer containing 40 bp of exon3 and ending in exon 6 (1.5 kb; Table 2). The two 1.5 kb PCR products were cloned, sequenced and ligated to a PGK:NEO selection cassette totaling 4.7 kb, similar to that of the FAH construct described in Example 1. The construct was sequenced and used for viral production.

TABLE 2

Primers used in the design of the rIL2rg construct

| Primer Location | Primer Sequence 5' to 3' | SEQ ID NO: |
| --- | --- | --- |
| 5'Rat IL2rg FOR | gtagcgaattcgcggccgctgattggattctcggtgtga | 17 |
| 5'Rat IL2rg REV | ggatagaattcgtcagtggctgcactcctggaatgtattatt | 18 |
| 3' Rat IL2rg FOR | gtagca agcttaggcgagccgaacagaagctaaac | 19 |
| 3' Rat IL2rg REV | ggataggtaccgcggccgcCAGGGATAAGCACAGCTTCC | 20 |

Example 4

Perfusion and Isolation of Hepatocytes from a Humanized Mouse

In this Example, human hepatocytes were isolated from a genetically modified mouse (the FRG KO mouse) repopulated with human hepatocytes. The human hepatocytes isolated from the mouse were used in the studies described in Example 5.

Hepatocytes were isolated from an in situ liver of a highly repopulated mouse (FRG knockout mouse model, Yecuris Corporation; see WO 2008/151283 and WO 2010/127275): albumin level=4.37 mg/mL, NTBC status: 0 mg/L) using a collagenase perfusion method. The mouse was first anaesthetized and then immobilized on a moisture-absorbing surface. The abdomen was opened and a cannula was inserted into the portal vein. The liver was then perfused with EBSS without calcium or magnesium, 10 mM Hepes pH 7.4 and 0.5 mM EDTA to blanch the liver and eliminate any blood clotting. Next the liver was perfused using a 1 mg/mL collagenase Type II solution in EBSS with calcium and magnesium and 10 mM Hepes pH 7.4 for 8 minutes until the liver was completely digested. The liver was then removed to a petri dish and dissociated using forceps and scissors to a homogenous slurry. Next, 5 mL of perfusion media (DMEM+10% fetal bovine serum) was used to deactivate the collagenase.

Using a sterile 25 mL pipet, the liver slurry was passed through a 100-micron filter into a 50 mL tube. The petri dish was then washed with perfusion media, passing it through the filter into the 50 mL tube. The volume in the tube was adjusted to 45 mL with perfusion media, and inverted two-three times to ensure a homogenous solution. The cell suspension was then passed through a 70-micron filter into a fresh 50 mL tube. The cells were centrifuged for 5 minutes at 140×g and 4° C. The supernatant was carefully aspirated and the cell pellet was resuspended in 10 mL of perfusion media. To dissociate any cell aggregates the cell suspension was passed through the 10 mL pipet for a total of five times. The suspension volume was adjusted to 45 mL with perfusion media. The cells were pelleted by centrifugation for 5 minutes at 140×g and 4° C. This is considered the first wash of the cell pellet. This step is repeated one more time. After the last centrifugation the cells were resuspended in 10 mL of perfusion media, passed through the pipet five times, and the volume adjusted to 45 mL with perfusion media. The cell suspension was then diluted 1:2 in perfusion media and counted with Trypan Blue in a hemocytometer chamber. The results are listed below:

| Mouse | Viable | Nonviable | Total | % Viable | # Viable of cells/mL | Total viable cells |
|---|---|---|---|---|---|---|
| 1338 | 297 | 19 | 316 | 94 | $3 \times 10^6$ | $135 \times 10^6$ |

Cells ($2.25 \times 10^6$) used for FACs analysis were transferred to a sterile 15 mL tube and the volume was adjusted to 10 mL with perfusion media.

| Mouse | Volume (mL) |
|---|---|
| 1338 | 0.75 |

The following cell numbers were removed for transplant into rats:

| # Cells/mouse | Total # of mice | Total mL | Total # cells |
|---|---|---|---|
| $1.00 \times 10^6$ | 15 | 3 mL | $15.00 \times 10^6$ |
| $3.00 \times 10^6$ | 17 | 17 mL | $51.00 \times 10^6$ |

The volumes were equalized between the two tubes. The cells were pelleted at 140×g for 5 minutes at 4° C. The supernatant was aspirated and the pellets were resuspended in the indicated volume of specified media:

| Purpose | Solution 1 | Volume | Total cell # |
|---|---|---|---|
| FACs | Perfusion media | 850 μL | $2.25 \times 10^6$ |
| $1.00 \times 10^6$ cells/mouse | HCM (Lonza, Cat # C3198) | 3.375 mL + 375 μL Anakinra | $15.00 \times 10^6$ |
| $3.00 \times 10^6$ cells/mouse | HCM (Lonza, Cat# C3198) | 3.825 mL + 425 μL Anakinra | $51.00 \times 10^6$ |

FACS Analysis to Determine % Human Hepatocytes:

4×200 μL of the cell suspension to be used for FACs analysis was dispensed into 1.5 mL microfuge tubes (each tube contained ~400,000 cells). The following primary antibodies were then added to each tube: #1=nothing, negative control; #2=2 μL of HLA ABC; #3=2 μL of OC2-2F8 and 2 μL of OC2-2G9; and #4=2 μL of HLA ABC, 2 μL of OC2-2F8 and 2 μL of OC2-2G9.

The solution was mixed by flicking the tubes, followed by incubating on ice for 30-60 minutes, with flicking every 5-10 minutes to keep cells suspended. The primary antibody was washed out by adding 1 mL of perfusion media to each tube and mixed by inversion several times. The cells were pelleted by centrifugation at 100×g for 3 minutes at 4° C. The supernatant was aspirated, followed by resuspending each cell pellet in 200 μL of a secondary antibody solution consisting of: 850 μL perfusion media; 8.5 μL Strept-APC; and 8.5 μL anti-rat PE. The solution was mixed by flicking the tubes, followed by incubating on ice for 30-60 minutes, with flicking every 5-10 minutes to keep cells suspended.

The secondary antibody was washed out by adding 1 mL of perfusion media to each tube, followed by mixing by inverting. The tubes were then centrifuged at 100×g for 3 minutes at 4° C., to pellet the cells, followed by aspirating the supernatant and resuspending each cell pellet in 200 μL of PI solution: 5 μL PI; 4 μL 0.5M EDTA; and 1 mL perfusion media. FACs analysis determined the percentage of repopulation by human hepatocytes in the mouse liver was 91%.

Example 5

Engraftment of Human Hepatocytes into Immunodeficient Rats

Liver humanization has not been successfully attempted in rats without the use of partial hepatectomy. In this example, Nude (RNU) rates were repopulated with human hepatocytes by injecting with Ad:uPa transplanted with human hepatocytes that contained Anakinra and treated with FK506, without a partial hepatectomy.

Forty nude rat pups (2 weeks old) were obtained from Charles River and acclimated for a week before the study began. The rats were assigned to + or −immunosuppressive groups, with controls in each group (see Table 3 below). Rats assigned to the +immunosuppressive group were treated with 2 mg/kg/day subcutaneous doses of FK506 (Tacrolimus) throughout the study, with the initial dosage being 20 μl of 5 mg/mL FK506 (i.p. injection) per day, based upon an average initial animal weight of 50 g at the start of the study. The −immunosuppression rats were not treated with FK506, but were injected subcutaneously with the same volume of saline throughout the study. All of the rats were then given an intravenous injection (retroorbital) of uPA adenovirus ($2.5 \times 10^9$ plaque forming units (PFU) per 50 g rat) 48-96 hours before hepatocyte injection.

Twenty-one days after the first dose of FK506 was administered the rats were then injected intrasplenically with placebo (PBS) or cell suspensions of human hepatocytes with Anakinra, according to Table 3 below, followed by post-operative administration of Buprenex stock at 1 µg/mL (5 µL/g) and Cetiofur at 1.25 mg/mL (200 µL). The human hepatocytes were perfused from humanized mouse livers as explained in Example 4.

TABLE 3

Animals and Cells

| Conditions | Total Cell Number | Rats + Immuno-suppression | Rats − Immuno-suppression |
|---|---|---|---|
| Control (0.2 mL PBS) | 0 | 3 | 3 |
| 5 × 10$^6$ cells/mL (0.2 mL) | 1 × 10$^6$ | 8 | 6 |
| 10 × 10$^6$ cells/mL (0.3 mL) | 3 × 10$^6$ | 8 | 7 |
| Total Rats | | 19 | 16 |
| Total Cells Needed | | 32 × 10$^6$ | 27 × 10$^6$ |

Twenty-four hours after hepatocyte injection, all of the rats were injected with Anakinra (10 µL/2510 µL/25 g), Buprenex (5 µL/g) and Ceftiofur at 1.25 mg/mL (200 µL), and then again at 48 hours post-op. Three days after surgery, 2 µL of blood was collected (saphenous-vein bleed) from each rat. The blood was diluted into 1 mL of ELISA buffer sample diluent. Samples were then tested for human serum albumin (hSA) by Quantitative human Albumin ELISA. This process was repeated weekly throughout the study. Analysis from the first ELISA showed that the average optical density reading (450 nm) of the experimental samples was twice that of the PBS injected controls. Both the −FK506 injected with 1×10$^6$ cells and +FK-506 injected with 3×10$^6$ cells had the highest optical density readings at 0.027. Though the range of human albumin levels fell below the linear range of the ELISA standard curve, the samples still exhibited detectable optical density readings for human albumin.

Two weeks after study commencement, the dose of FK506 was increased to 30 µl of 5 mg/mL due to an increase in animal weight. Four weeks after study commencement, the dose of FK506 was again increased to 25 µl of 10 mg/mL to account for growth of the rats.

Four weeks after hepatocyte injection (~5 weeks after study commencement), at least 50 µl of whole blood was collected from the rats and allowed to clot for 1 hour at room temperature. Serum was collected by centrifuging the whole blood at 1,500 rpm×15 minutes. The serum was then diluted 1:25 and 1:50 and used for hSA testing via ELISA. Five µl of whole blood was also taken from 6 random rats in the +FK506 treatment group. Five animals tested positive for human albumin between the ranges of 12 and 70 ng/mL with serum. One whole blood sample (#33) tested positive for human albumin at 220 ng/mL. The rats were also reweighed and it was found that the +immunosuppressed rats were significantly smaller than their non-treated counterparts, therefore the administration of FK506 was changed to every other day.

Eight weeks after hepatocyte injection, 5 µl of whole blood was taken from each animal for ELISAs. The blood was immediately diluted in 1 mL of sample buffer for a dilution of 1:200. Rat #29 (3×10$^6$; +FK506 group) tested positive for hSA in all replicates. Results were confirmed by an independent blind repeat.

Almost nine weeks after hepatocyte injection, all animals were sacrificed. Cardiac punctures and exsanguinations were performed to obtain whole blood and serum for ELISAs. Animals were first dosed with 500 µL of a ketamine cocktail before cardiac puncture. Portions of the spleen and liver (lobe 6) were flash frozen for genomic DNA isolation and detection of human genes. The remaining liver and spleen portions were then fixed in 10% normal buffered formalin for 48 hours, at which time they were transferred to 70% ethanol prior to paraffin embedding. Liver sections were stained with FAH antibody to identify the human hepatocytes. A humanized FRG KO mouse liver was used as a control. Tissues were analyzed for histologic evaluation and staining. The results are shown in FIG. 7. Sections were generated from a control liver and spleen as well as the liver and spleen from rat #29. The images show that the liver from rat #29 contained positive human hepatocytes by staining with human specific FAH antibody. These sections are similar to the engraftment observed in the confirmed FAH mouse model with the same antibody.

The initial ELISA data demonstrated the presence of human serum albumin in the engrafted nude rats. The data obtained from subsequent ELISA analyses, as well as the positive IHC indicate that a population of human cells were able to engraft into nude rats treated with uPA, Anakinra, and FK506. The levels of human albumin (~1.5 µg/mL) relate to 10,000 hepatocytes in the liver being human hepatocytes.

Example 6

Fah-Deficient Rats

Figure 8:
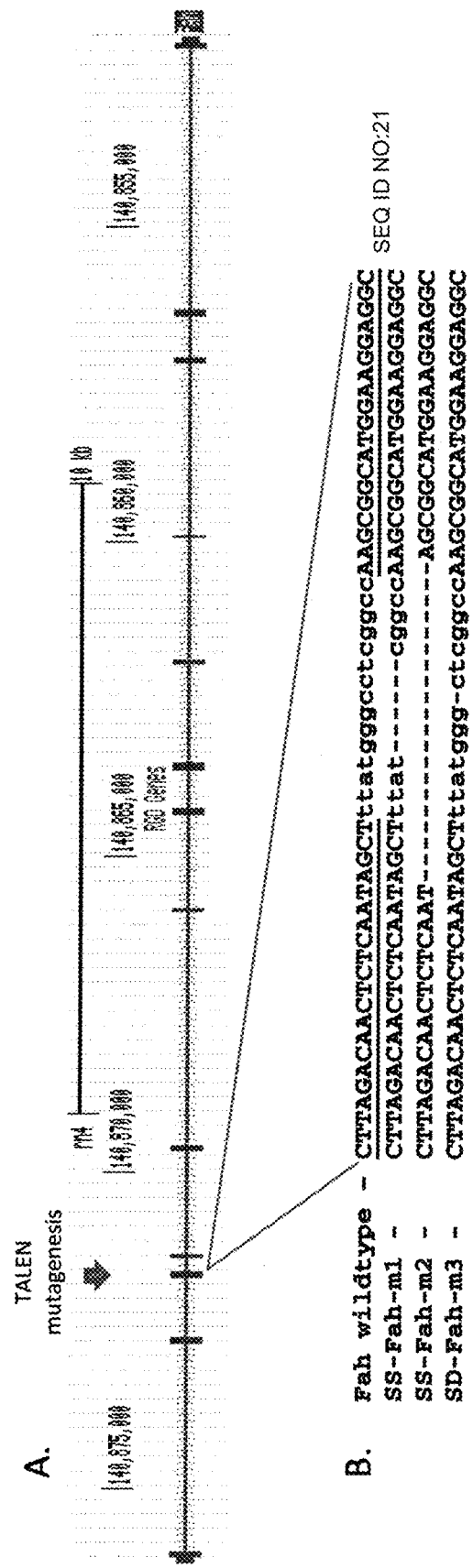
FIG. 8 is (A) a schematic of a pair of TALENs designed to target and disrupt sequences in exon 3 of the rat Fah gene (GenBank Accession NM_017181); (B) the wild-type TALEN target sequence with specific TALEN binding sites underlined and in capital letters (SEQ ID NO:21)

Rats (Sprague Dawley strain) with mutations in the highly conserved Fah gene were generated using Transcriptional Activator-Like Effector Nucleases (TALENs) designed to target the endogenous *Rattus norvegicus* Fah gene exon 3 sequence (SEQ ID NO:21; FIG. 8), where the underlined portions of the sequence are the target binding sequences of two TALEN monomers, on opposite DNA strands, separated by the lowercase sequence where the TALEN heterodimer-mediated cleavage occurs. Standard microinjection of the male pronucleus of rat embryos from the Dahl SS (SS; SS/JrHsdMcwi) and Sprague Dawley (SD; SD/Crl) with an equimolar mixture of two in vitro-transcribed mRNAs encoding each TALEN monomer at a final concentration of 10 ng/µL led to the identification of three founders with putative disruptive mutations in the Fah gene using the Surveyor Nuclease Mutation Detection kit (Transgenomic, Inc) as previously described (Geurts, A. M. et al. Generation of gene-specific mutated rats using zinc-finger nucleases. *Methods Mol Biol* 597, 211-25 (2010)).

Disruption of the rat Fah target gene was confirmed using Sanger sequencing and all three mutant animal alleles were evidenced by micro deletions (1-20 base pairs) of coding sequence within exon 3 (FIG. 8(b)). Three mutant alleles were identified (Fah-m1, Fah-m2 and Fah-m3). Fah-m1 (6-bp deletion) and Fah-m2 (20-bp deletion) were generated in the SS while Fah-m3 (1-bp deletion) was identified in the SD rat strain genetic backgrounds. Two mutations (Fah-m2 and Fah-m3) cause a frameshift in the nascent gene transcript shifting the natural open reading frame after Serine 69 or Glycine 73, respectively, and truncation of the protein product via the insertion of stop codons into the reading frame after amino acids 91 and 120, respectively. The Fah-m1 mutation results in a loss of three amino acids and insertion of one amino acid (Methionine 71-Glycine 72-Lysine 73) and insertion of an isoleucine residue (FIG. 9; SEQ ID NOS:22-25) from these founders, three colonies of mutant animals (SS-Fah-m1, SS-Fah-m2 and SD-Fah-m3) were established by backcross and intercross of heterozygous carriers.

Figure 12:
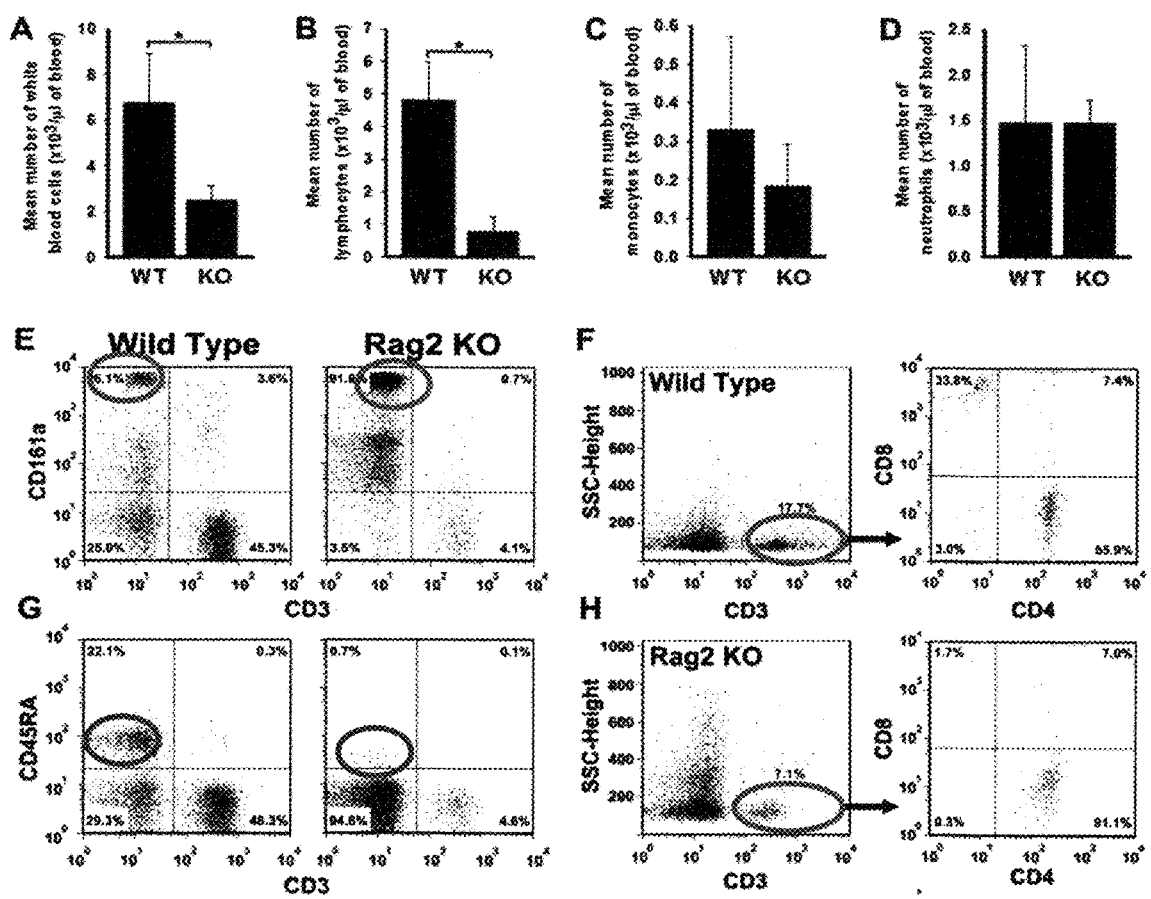

Mutations in the Il2rg and Rag2 genes were generated in similar fashion in both genetic backgrounds. Target sequences and alleles are shown in FIG. 10 (SEQ ID NOS:26-27). All mutations were predicted to be frame-shift truncations of the target gene. Knockout of both genes on the SS genetic background leads to severe immune deficiency of T- and B-cell populations in both strains and NK-cell populations are diminished in the SS-Il2rg-ml strain (FIGS. 11-12).

Figures 13, 14:
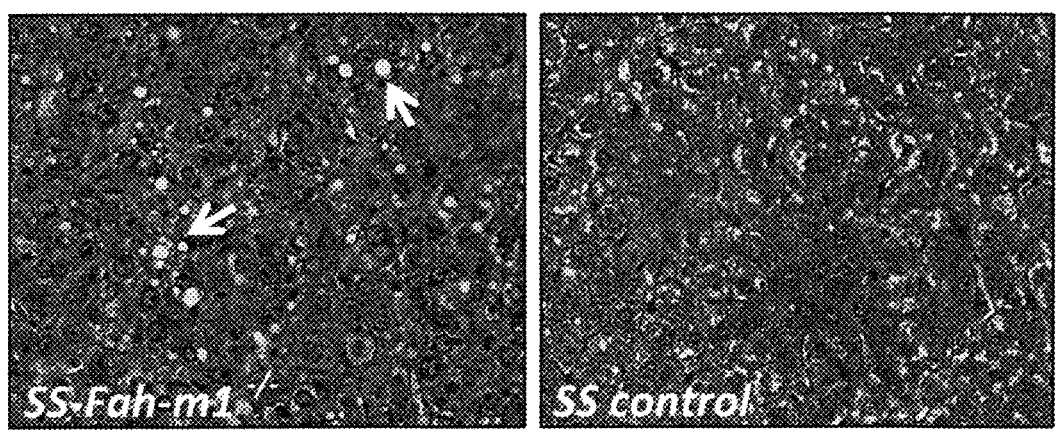
FIG. 13 is a table of genotypes of live born rat pups from Fah heterozygous breedings.
FIG. 14 is Trichrome staining of fixed tissue from a 9-week old SS-Fah-m1$^{-/-}$ after 8 days of NTBC withdrawal showing evidence of early stages of liver dysfunction evident as (arrows) compared to a control SS inbred animal of a similar age on NTBC.

Disruption of Fah in the rat for all three alleles leads to embryonic lethality as no homozygous offspring are observed in intercrosses of heterozygous animals in the absence of any treatment. Administering NTBC to the drinking water of breeding heterozygotes (8 mg/mL), however, can rescue the lethal effects of these mutations at Mendelian or near-Mendelian ratios, depending on the allele (FIG. 13), demonstrating that this drug can protect mutant rat embryos from the embryonic lethality. SS-Fah-m1 null animals maintained on NTBC in their drinking water are healthy and are reproductively fit. The Table in FIG. 13 shows the genotypes of live born rat pups from heterozygous breedings. The number of pups with each genotype expected from Mendellian ratios is shown, along with the actually observed numbers in red. Without NTBC treatment during pregnancy, no homozygous mutant pups were born. Addition of NTBC to the drinking water of the mothers resulted in the birth of mutant embryos with both Fah-m1 and Fah-m2 breeders.

Withdrawal of NTBC from an adult animal SS-Fah-m1 animal, but otherwise ad libitum access to food and water, leads to a rapid decline in body weight (>20% loss in 7-8 days). Examination of fixed liver tissue by sections and trichrome staining (FIG. 14) revealed marked vacuolization and enlargement of the hepatocytes. In addition, necrotic hepatocytes are seen in high numbers, whereas none were seen in the control, NTBC-treated littermate. Similarly, the kidneys showed extensive injury, especially cystic dilatation of the tubules, after NTBC withdrawal (FIG. 15). These histological findings are typical for Fah deficiency in rodents.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method of expanding human hepatocytes in vivo, comprising:
    transplanting human hepatocytes into a first rat, wherein:
        said first rat is a genetically modified fumarylacetoacetate hydrolase (Fah)-deficient rat whose genome is homozygous for a disruption in exon 3 of the Fah gene such that the disruption results in loss of expression of functional FAH protein and decreased liver function in the first rat,
        and allowing the human hepatocytes to expand in the first rat, thereby expanding human hepatocytes in vivo.

2. The method of claim 1, wherein the human hepatocytes transplanted into the first rat are isolated human hepatocytes.

3. The method of claim 2, wherein the human hepatocytes are isolated from the liver of a humanized non-human mammal prior to transplanting into the first rat, wherein the non-human mammal is an FRG KO mouse.

4. The method of claim 1, further comprising inducing acute liver damage in the first rat prior to transplanting the human hepatocytes.

5. The method of claim 1, further comprising administering a vector encoding urokinase to the first rat prior to transplanting the human hepatocytes.

6. The method of claim 1, wherein the Fah-deficient rat genome is further homozygously disrupted at the IL2rg (ILrg−/−) locus and at the Rag1 (Rag1−/−) or Rag2 (Rag2−/−) loci, wherein the rat is immunosuppressed.

7. The method of claim 1, wherein the first rat is an immunodeficient rat, wherein the immunodeficiency is due to one or more genetic alterations that inhibit the development of functional immune cells, wherein the one or more genetic alterations is selected from the group consisting of selected from the group consisting of Rag1 deficiency, Rag2 deficiency, Il2rg deficiency, SCID, Sirp-$\alpha^{hum/hum}$, nude, perforin$^{-/-}$, and combinations thereof.

8. The method of claim 1, the method further comprising administering one or more immunosuppressive agents to the first Fah-deficient rat prior to transplanting the human hepatocytes.

9. The method of claim 8, wherein the one or more immunosuppressive agents are selected from the group consisting of FK506, cyclosporin A, fludarabine, mycophenolate, prednisone, rapamycin, azathioprine, and combinations thereof.

10. The method of claim 1, further comprising collecting the expanded human hepatocytes from the first rat.

11. The method of claim 10, further comprising expanding the collected human hepatocytes by serial transplantation.

12. The method of claim 1, wherein said first rat is immunodeficient, wherein the immunodeficiency is due to a genetic alteration, immunosuppression, or a combination thereof.

13. The method of claim 12, wherein the Fah-deficient rat genome is further homozygously disrupted at the IL2rg (ILrg−/−) locus, at the Rag1 (Rag1−/−) locus, at the Rag2 (Rag2−/−) locus, or a combination thereof.

14. The method of claim 11, wherein said serial transplantation comprises:
    transplanting the collected expanded human hepatocytes from the first rat into a second rat wherein:
        said second rat is a genetically modified Fah-deficient rat whose genome is homozygous for a disruption in the Fah gene such that the disruption results in loss of expression of functional FAH protein and decreased liver function, or said second rat is an immunodeficient rat with a liver injury, wherein the immunodeficiency of the rat is due to a genetic alteration, immunosuppression, or a combination thereof; and allowing the human hepatocytes to expand in said second rat, thereby further expanding the human hepatocytes in vivo.

* * * * *

SEQUENCE LISTING

```
<160> NUMBER OF SEQ ID NOS: 29

<210> SEQ ID NO 1
<211> LENGTH: 82
<212> TYPE: DNA
<213> ORGANISM: Rattus norvegicus

<400> SEQUENCE: 1
gggcctcggc caagcggcat ggtgaaagga ggcaagagca tctttacaga acttactgtc      60
tgccagccaa gcccagctca ga                                              82

<210> SEQ ID NO 2
<211> LENGTH: 4657
<212> TYPE: DNA
<213> ORGANISM: Artificial Sequence
<220> FEATURE:
<223> OTHER INFORMATION: Synthetic construct

<400> SEQUENCE: 2
gcggccgcgt agcaagcttc tgtgaggtca gagaccagcc ttgacaagat attgggcctc      60
tgtgttcatt tgaatccatg cagagctctt acagtgcata aaagaaatcc attcatttgg    120
tctgagcact gtgccttctg cagttcccta cggcctgagc tctgctgcat ttaagctacc    180
acagagctga tactccaagt tactacatgt gtaacactca ctgctctgct tcataagaga    240
atggccctga gcaaagccct gggccgagca tgaaaagagg ttcgggttct tggtaaggtg    300
atgagcaact cataactaga gatcatggct ctgctttctt tcttgtcctg gatcccgtct    360
caatggaatc catgagtccc taagtaactg tgctgtgact gtcagaactg actgtcactc    420
ttctcctagc caaagccacg gattggtgtg gccatcggtg accagatctt ggacctgagt    480
gtcattaaac acctctttac cggacctgtc ctctccaaac atcagcatgt cttcgatgag    540
gtaggacatt gtgtcatgga ctgtctctgt ctcaccacct actacaaatg acatagcatc    600
ttcatagtca ccagttattc ccggatgagg aggagctgtt ctgagacaca caggtggcat    660
```

```
gaggtagcct cgacacctta gggcagcttc tcaatagaat gtgagctcct gagtccagtg    720
gatctctcca agttgcctat gaggtgagac tgttgtgtta gcctggttcc tttatataca    780
aggatgttca tgcttttggtc tttggaggct caggaaaacc ttgagaaaag gagccatgag    840
ccttgcagtc tagattttag ggtaaagctt gagacactca tcctggcttc tatgttcatg    900
aatgatgact gcccagtact tcaagggtac agtcctgggg catccaacct tgcttgtgtg    960
tctgtgtagg atgcctaccc tgtcatccag gtatgcagtt gtgcctgggg gcagccagct   1020
tgtctacctc gtctgtgtgg gatggatgta actttcctcc cttgtcacag ctcagctctt   1080
agggtctgct tttcccctgaa acacaggcag ggatagttgt ggtatttacc aagtacctct   1140
tctgttcagg agctttgcat gaatcctttc tgccagtcct cctggccacc ctctgctaca   1200
gagccggcat tgttgctaga taagtgggac ttgtacagtt caagagttgc tgtctgcata   1260
ataataattg attgtgagat gtaaatccag aagtggatgg gacatcaggg gaggtgacag   1320
ctttctccag ctctaagcag agagggcaaa atgtaaacaa aggtcccaac ttgtgaatgg   1380
atgcagagaa gtcaggctga caggagggat ggtctagggg ttttctcagg tacaacctct   1440
tctattcctg ttttggtctt agacaactct caatagcttt atgggcctcg gccaagcggc   1500
atggtgacga attctgatct accgggtagg ggaggcgctt ttcccaaggc agtctggagc   1560
atgcgcttta gcagcccgc tgggcacttg gcgctacaca agtggcctct ggcctcgcac   1620
acattccaca tccaccggta ggcgccaacc ggctccgttc tttggtggcc ccttcgcgcc   1680
accttctact cctcccctag tcaggaagtt ccccccccgcc ccgcagctcg cgtcgtgcag   1740
gacgtgacaa atggaagtag cacgtctcac tagtctcgtg cagatggaca gcaccgctga   1800
gcaatgaaag cgggtaggcc tttggggcag cggccaatag cagctttgct ccttcgcttt   1860
ctgggctcag aggctgggaa ggggtgggtc cggggcggg ctcaggggcg ggctcagggg   1920
cggggcgggc gcccgaaggt cctccggagg cccggcattc tgcacgcttc aaaagcgcac   1980
gtctgccgcg ctgttctcct cttcctcatc tccgggcctt tcgacctgca gccaatatgg   2040
gatcggccat tgaacaagat ggattgcacg caggttctcc ggccgcttgg gtggagaggc   2100
tattcggcta tgactgggca caacagacaa tcggctgctc tgatgccgcc gtgttccggc   2160
tgtcagcgca ggggcgcccg gttctttttg tcaagaccga cctgtccggt gccctgaatg   2220
aactgcagga cgaggcagcg cggctatcgt ggctggccac gacgggcgtt ccttgcgcag   2280
ctgtgctcga cgttgtcact gaagcgggaa gggactggct gctattgggc gaagtgccgg   2340
ggcaggatct cctgtcatct caccttgctc ctgccgagaa agtatccatc atggctgatg   2400
caatgcggcg gctgcatacg cttgatccgg ctacctgccc attcgaccac caagcgaaac   2460
atcgcatcga gcgagcacgt actcggatgg aagccggtct tgtcgatcag gatgatctgg   2520
acgaagagca tcaggggctc gcgccagccg aactgttcgc caggctcaag gcgcgcatgc   2580
ccgacggcga tgatctcgtc gtgacccatg gcgatgcctg cttgccgaat atcatggtgg   2640
aaaatggccg cttttctgga ttcatcgact gtggccggct gggtgtggcg gaccgctatc   2700
aggacatagc gttggctacc cgtgatattg ctgaagagct tggcggcgaa tgggctgacc   2760
gcttcctcgt gctttacggt atcgccgctc ccgattcgca gcgcatcgcc ttctatcgcc   2820
ttcttgacga gttcttctga ggggatcaat tctctagagc tcgctgatca gcctcgactg   2880
tgccttctag ttgccagcca tctgttgttt gcccctcccc cgtgccttcc ttgaccctgg   2940
aaggtgccac tcccactgtc ctttcctaat aaaatgagga aattgcatcg cattgtctga   3000
```

```
gtaggtgtca ttctattctg gggggtgggg tggggcagga cagcaagggg gaggattggg      3060
aagacaatag caggcatgct ggggatgcgg tgggctctat ggcttctgag gcggaaagaa      3120
ccagctgggg ctcgagatcc actagttcta aagcttgcca gccaagccca gctcagagat      3180
gacaaggagc ttcggcagcg gtgagaatac atggaaagag tgtcatgtca ggggagatta      3240
ggcctgggta gttggcagta cccttctgca tgactgcttg gttacttgtc tatctatcct      3300
ggtacagtca ggcccactcc atccatcccc acagctgggt tgcatgctgg tgggaggtgt      3360
ctgggcctgg aagactggat gaagctcctg attctgtgtt tcagtgcatt cacctcccag      3420
gcttctgcca cgatgcacct tcctgctacc ataggtgagt cctgattccc tgctttgcca      3480
acccgaatag cttagtgggc ctagatagct agacagatgt gttggaaccc catatcttgg      3540
tggagagaaa acagatcaag agctccagga ttgccagctg atcccaatgt gaccaagctc      3600
atggaatagt gagccttggc tcagttgtca caagcctgct ctcccagagc agcagcctaa      3660
gttttttact acctgcatgg ataccgtat agcaatttgc ttcatcttcc cagattttga       3720
ggtaagcact ttgagcagtc aggagagagg tgttttgagg aaaaccacag gaccctgcag      3780
ggagcatgta tacatttgac caggcatttg gtttgactga ttcagcaagt tgctgtcagt      3840
atagtttcat agcctgaagc aggtttaggc tgcttcatct cagtatgaca gcaatgaggg      3900
gaagcctttg ctcttgcctg ggcacctgtg gtctgagaac tgtatagctt tgctgtggga      3960
agatggagtt tcttgaacaa gtctccccat tcaacaaaac ctttcagagg tgctggtagc      4020
caacagctag gcagaaggtg ggcttgagga tgggctcctc tcttgcttct ctataggact      4080
gtgctatgtg ttttttatag caagccgttt gttttctagg gatccttcat ccttcccagg      4140
tcactgatgc tgtagcctct tgttttact gttatggatg tgattactct tatgataaat       4200
agtctcactg ttatctctgt ccacaggact gaaggtggga agtagtaagc acagctcaga      4260
ctgtctgcct tttgcttagc tggctcccag acactgtttc ctctccttat tctgccgctt      4320
atacttctag tccaggcgct ggggttgggg tactcagctt tgctttgtgg gaggatgcag      4380
aaggtttagg aagatgagta agcaaactag cctaaatgga ttttctagta gaacttagta      4440
actcacatat ggggagggat atctgctgtc catgaacccc caagttcagc tcatcacaat      4500
caacagacac tgatagacaa gttcaaatac aaaggcaaga tgctttattc taggtgctaa      4560
ggggcaggca catgacatga gagctgaacc aggacttccg ggaatggtga cattgagcaa      4620
aagtctccat acatggaact agaggtcgcg gccgcgg                              4657

<210> SEQ ID NO 3
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 3
gtagcgaatt cgcggccgcg ctgtgaggtc agagaccagc c                          41

<210> SEQ ID NO 4
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 4
ggatagaatt cgtcaccatg ccgcttggcc gaggccc                               37
```

<210> SEQ ID NO 5
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 5
gtagcaagct tgccagccaa gcccagctca ga                                   32

<210> SEQ ID NO 6
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 6
ggataggtac cgcggccgcg acctctagtt ccatgtatgg                           40

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
gaggccttgt tcacacatga                                                 20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
ctaaagcgca tgctccagac                                                 20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
attgcatcgc attgtctgag                                                 20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
agtctcctgc agagggaaca                                                 20

<210> SEQ ID NO 11
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 11
tgctcctgcc gagaaagtat                                          20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
caacagatgg ctggcaacta                                          20

<210> SEQ ID NO 13
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 13
gtagcgaatt cgcggccgcg ctgtgaggtc agagaccagc c                  41

<210> SEQ ID NO 14
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 14
tagtcgacgt caaggatgct cttgcctcct                               30

<210> SEQ ID NO 15
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 15
gcaggtggtg ccacttgtcc ccagttgagg                               30

<210> SEQ ID NO 16
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 16
gtatgcatat cgatggaatt cccctttcca                               30

<210> SEQ ID NO 17
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 17
gtagcgaatt cgcggccgct gattggattc tcggtgtga                     39

```
<210> SEQ ID NO 18
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 18
ggatagaatt cgtcagtggc tgcactcctg aatgtatta tt                              42

<210> SEQ ID NO 19
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 19
gtagcaagct taggcgagcc gaacagaagc taaac                                    35

<210> SEQ ID NO 20
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 20
ggataggtac cgcggccgcc agggataagc acagcttcc                                39

<210> SEQ ID NO 21
<211> LENGTH: 55
<212> TYPE: DNA
<213> ORGANISM: Rattus norvegicus

<400> SEQUENCE: 21
cttagacaac tctcaatagc tttatgggcc tcggccaagc ggcatggaag gaggc              55

<210> SEQ ID NO 22
<211> LENGTH: 419
<212> TYPE: PRT
<213> ORGANISM: Rattus norvegicus

<400> SEQUENCE: 22

Met Ser Phe Ile Pro Val Ala Glu Asp Ser Asp Phe Pro Ile Gln Asn
1               5                   10                  15

Leu Pro Tyr Gly Val Phe Ser Thr Gln Ser Asn Pro Lys Pro Arg Ile
            20                  25                  30

Gly Val Ala Ile Gly Asp Gln Ile Leu Asp Leu Ser Val Ile Lys His
        35                  40                  45

Leu Phe Thr Gly Pro Val Leu Ser Lys His Gln His Val Phe Asp Glu
    50                  55                  60

Thr Thr Leu Asn Ser Phe Met Gly Leu Gly Gln Ala Ala Trp Lys Glu
65                  70                  75                  80

Ala Arg Ala Ser Leu Gln Asn Leu Leu Ser Ala Ser Gln Ala Gln Leu
                85                  90                  95

Arg Asp Asp Lys Glu Leu Arg Gln Arg Ala Phe Thr Ser Gln Ala Ser
            100                 105                 110

Ala Thr Met His Leu Pro Ala Thr Ile Gly Asp Tyr Thr Asp Phe Tyr
        115                 120                 125

Ser Ser Leu Gln His Ala Thr Asn Val Gly Ile Met Phe Arg Gly Lys
    130                 135                 140
```

```
Glu Asn Ala Leu Leu Pro Asn Trp Leu His Leu Pro Val Gly Tyr His
145                 150                 155                 160

Gly Arg Ala Ser Ser Val Val Ser Gly Thr Pro Ile Arg Arg Pro
            165                 170                 175

Met Gly Gln Met Arg Pro Asp Asn Ser Lys Pro Pro Val Tyr Gly Ala
            180                 185                 190

Ser Lys Arg Leu Asp Met Glu Leu Glu Met Ala Phe Phe Val Gly Pro
            195                 200                 205

Gly Asn Arg Phe Gly Glu Pro Ile Pro Ile Ser Lys Ala Gln Glu His
210                 215                 220

Ile Phe Gly Met Val Leu Met Asn Asp Trp Ser Ala Arg Asp Ile Gln
225                 230                 235                 240

Gln Trp Glu Tyr Val Pro Leu Gly Pro Phe Leu Gly Lys Ser Phe Gly
            245                 250                 255

Thr Thr Ile Ser Pro Trp Val Val Pro Met Asp Ala Leu Met Pro Phe
            260                 265                 270

Val Val Pro Asn Pro Lys Gln Asp Pro Lys Pro Leu Pro Tyr Leu Cys
            275                 280                 285

His Ser Gln Pro Tyr Thr Phe Asp Ile Asn Leu Ser Val Ala Leu Lys
            290                 295                 300

Gly Glu Gly Met Ser Gln Ala Ala Thr Ile Cys Arg Ser Asn Phe Lys
305                 310                 315                 320

His Met Tyr Trp Thr Ile Leu Gln Gln Leu Thr His His Ser Val Asn
            325                 330                 335

Gly Cys Asn Leu Arg Pro Gly Asp Leu Leu Ala Ser Gly Thr Ile Ser
            340                 345                 350

Gly Ser Asp Pro Glu Ser Phe Gly Ser Met Leu Glu Leu Ser Trp Lys
            355                 360                 365

Gly Thr Lys Ala Ile Asp Val Gly Gln Gly Gln Thr Arg Thr Phe Leu
370                 375                 380

Leu Asp Gly Asp Glu Val Ile Ile Thr Gly His Cys Gln Gly Asp Gly
385                 390                 395                 400

Tyr Arg Val Gly Phe Gly Gln Cys Ala Gly Lys Val Leu Pro Ala Leu
            405                 410                 415

Ser Pro Ala

<210> SEQ ID NO 23
<211> LENGTH: 417
<212> TYPE: PRT
<213> ORGANISM: Rattus norvegicus

<400> SEQUENCE: 23

Met Ser Phe Ile Pro Val Ala Glu Asp Ser Asp Phe Pro Ile Gln Asn
1               5                   10                  15

Leu Pro Tyr Gly Val Phe Ser Thr Gln Ser Asn Pro Lys Pro Arg Ile
            20                  25                  30

Gly Val Ala Ile Gly Asp Gln Ile Leu Asp Leu Ser Val Ile Lys His
            35                  40                  45

Leu Phe Thr Gly Pro Val Leu Ser Lys His Gln His Val Phe Asp Glu
            50                  55                  60

Thr Thr Leu Asn Ser Phe Ile Gly Gln Ala Ala Trp Lys Glu Ala Arg
65                  70                  75                  80

Ala Ser Leu Gln Asn Leu Leu Ser Ala Ser Gln Ala Gln Leu Arg Asp
            85                  90                  95
```

```
Asp Lys Glu Leu Arg Gln Arg Ala Phe Thr Ser Gln Ala Ser Ala Thr
            100                 105                 110

Met His Leu Pro Ala Thr Ile Gly Asp Tyr Thr Asp Phe Tyr Ser Ser
            115                 120                 125

Leu Gln His Ala Thr Asn Val Gly Ile Met Phe Arg Gly Lys Glu Asn
            130                 135                 140

Ala Leu Leu Pro Asn Trp Leu His Leu Pro Val Gly Tyr His Gly Arg
145                 150                 155                 160

Ala Ser Ser Val Val Val Ser Gly Thr Pro Ile Arg Arg Pro Met Gly
                165                 170                 175

Gln Met Arg Pro Asp Asn Ser Lys Pro Pro Val Tyr Gly Ala Ser Lys
            180                 185                 190

Arg Leu Asp Met Glu Leu Glu Met Ala Phe Phe Val Gly Pro Gly Asn
            195                 200                 205

Arg Phe Gly Glu Pro Ile Pro Ile Ser Lys Ala Gln Glu His Ile Phe
            210                 215                 220

Gly Met Val Leu Met Asn Asp Trp Ser Ala Arg Asp Ile Gln Gln Trp
225                 230                 235                 240

Glu Tyr Val Pro Leu Gly Pro Phe Leu Gly Lys Ser Phe Gly Thr Thr
                245                 250                 255

Ile Ser Pro Trp Val Val Pro Met Asp Ala Leu Met Pro Phe Val Val
            260                 265                 270

Pro Asn Pro Lys Gln Asp Pro Lys Pro Leu Pro Tyr Leu Cys His Ser
            275                 280                 285

Gln Pro Tyr Thr Phe Asp Ile Asn Leu Ser Val Ala Leu Lys Gly Glu
            290                 295                 300

Gly Met Ser Gln Ala Ala Thr Ile Cys Arg Ser Asn Phe Lys His Met
305                 310                 315                 320

Tyr Trp Thr Ile Leu Gln Gln Leu Thr His His Ser Val Asn Gly Cys
                325                 330                 335

Asn Leu Arg Pro Gly Asp Leu Leu Ala Ser Gly Thr Ile Ser Gly Ser
            340                 345                 350

Asp Pro Glu Ser Phe Gly Ser Met Leu Glu Leu Ser Trp Lys Gly Thr
            355                 360                 365

Lys Ala Ile Asp Val Gly Gln Gly Gln Thr Arg Thr Phe Leu Leu Asp
            370                 375                 380

Gly Asp Glu Val Ile Ile Thr Gly His Cys Gln Gly Asp Gly Tyr Arg
385                 390                 395                 400

Val Gly Phe Gly Gln Cys Ala Gly Lys Val Leu Pro Ala Leu Ser Pro
                405                 410                 415

Ala

<210> SEQ ID NO 24
<211> LENGTH: 91
<212> TYPE: PRT
<213> ORGANISM: Rattus norvegicus

<400> SEQUENCE: 24

Met Ser Phe Ile Pro Val Ala Glu Asp Ser Asp Phe Pro Ile Gln Asn
1               5                   10                  15

Leu Pro Tyr Gly Val Phe Ser Thr Gln Ser Asn Pro Lys Pro Arg Ile
            20                  25                  30

Gly Val Ala Ile Gly Asp Gln Ile Leu Asp Leu Ser Val Ile Lys His
            35                  40                  45
```

```
Leu Phe Thr Gly Pro Val Leu Ser Lys His Gln His Val Phe Asp Glu
    50                  55                  60

Thr Thr Leu Asn Ser Gly Met Glu Gly Gly Lys Ser Ile Leu Thr Glu
65                  70                  75                  80

Leu Thr Val Cys Gln Pro Ser Pro Ala Gln Arg
                85                  90
```

<210> SEQ ID NO 25
<211> LENGTH: 120
<212> TYPE: PRT
<213> ORGANISM: Rattus norvegicus

<400> SEQUENCE: 25

```
Met Ser Phe Ile Pro Val Ala Glu Asp Ser Asp Phe Pro Ile Gln Asn
1               5                   10                  15

Leu Pro Tyr Gly Val Phe Ser Thr Gln Ser Asn Pro Lys Pro Arg Ile
                20                  25                  30

Gly Val Ala Ile Gly Asp Gln Ile Leu Asp Leu Ser Val Ile Lys His
            35                  40                  45

Leu Phe Thr Gly Pro Val Leu Ser Lys His Gln His Val Phe Asp Glu
    50                  55                  60

Thr Thr Leu Asn Ser Phe Met Gly Ser Ala Lys Arg His Gly Arg Arg
65                  70                  75                  80

Gln Glu His Pro Tyr Arg Thr Tyr Cys Leu Pro Ala Lys Pro Ser Ser
                85                  90                  95

Glu Met Thr Arg Ser Phe Gly Ser Val His Ser Pro Arg Leu Leu
            100                 105                 110

Pro Arg Cys Thr Phe Leu Leu Pro
        115                 120
```

<210> SEQ ID NO 26
<211> LENGTH: 55
<212> TYPE: DNA
<213> ORGANISM: Rattus norvegicus

<400> SEQUENCE: 26
ctcagtgttc ctactctgcc cctcccagag gttcaatgct ttgtgttcaa tgtcg     55

<210> SEQ ID NO 27
<211> LENGTH: 58
<212> TYPE: DNA
<213> ORGANISM: Rattus norvegicus

<400> SEQUENCE: 27
atgtcagaag cattctattt ctatatgttg agatgctctg aagataattc gagtgagg     58

<210> SEQ ID NO 28
<211> LENGTH: 26
<212> TYPE: PRT
<213> ORGANISM: Rattus norvegicus

<400> SEQUENCE: 28

```
Ala Ser Ala Lys Arg His Gly Glu Arg Arg Gln Glu His Leu Tyr Arg
1               5                   10                  15

Thr Tyr Cys Leu Pro Ala Lys Pro Ser Ser
                20                  25
```

<210> SEQ ID NO 29
<211> LENGTH: 153

-continued

```
<212> TYPE: PRT
<213> ORGANISM: Artificial Sequence
<220> FEATURE:
<223> OTHER INFORMATION: Synthetic polypeptide

<400> SEQUENCE: 29

Met Arg Pro Ser Gly Arg Lys Ser Lys Met Gln Ala Phe Arg Ile
1               5                   10                  15

Trp Asp Val Asn Gln Lys Thr Phe Tyr Leu Arg Asn Asn Gln Leu Val
            20                  25                  30

Ala Gly Tyr Leu Gln Gly Pro Asn Val Asn Leu Glu Glu Lys Ile Asp
        35                  40                  45

Val Val Pro Ile Glu Pro His Ala Leu Phe Leu Gly Ile His Gly Gly
    50                  55                  60

Lys Met Cys Leu Ser Cys Val Lys Ser Gly Asp Glu Thr Arg Leu Gln
65                  70                  75                  80

Leu Glu Ala Val Asn Ile Thr Asp Leu Ser Glu Asn Arg Lys Gln Asp
                85                  90                  95

Lys Arg Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala
        115                 120                 125

Asp Gln Pro Val Ser Leu Thr Asn Met Pro Asp Glu Gly Val Met Val
    130                 135                 140

Thr Lys Phe Tyr Phe Gln Glu Asp Glu
145                 150
```